(12) United States Patent
Wood et al.

(10) Patent No.: US 9,096,836 B2
(45) Date of Patent: Aug. 4, 2015

(54) LIQUID MICROORGANISM CONSORTIA FORMULATION

(71) Applicant: Sustainable Community Development, L.L.C., Kansas City, MO (US)

(72) Inventors: Matthew Wood, Kansas City, MO (US); Narin Tipsrisukond, Kansas City, MO (US)

(73) Assignee: SUSTAINABLE COMMMUNITY DEVELOPMENT, L.L.C., Kansas City, MO (US)

(*) Notice: Subject to any disclaimer, the term of this patent is extended or adjusted under 35 U.S.C. 154(b) by 0 days.

(21) Appl. No.: 13/826,286

(22) Filed: Mar. 14, 2013

(65) Prior Publication Data

US 2013/0202562 A1    Aug. 8, 2013

Related U.S. Application Data

(63) Continuation-in-part of application No. 13/304,280, filed on Nov. 23, 2011, now abandoned.

(51) Int. Cl.
| | |
|---|---|
| *C12N 1/38* | (2006.01) |
| *C12N 1/20* | (2006.01) |
| *A01N 63/00* | (2006.01) |
| *A23K 1/00* | (2006.01) |
| *A23L 1/30* | (2006.01) |
| *C12P 1/04* | (2006.01) |

(52) U.S. Cl.
CPC ...... *C12N 1/20* (2013.01); *A01N 63/00* (2013.01); *A23K 1/008* (2013.01); *A23K 1/009* (2013.01); *A23L 1/3014* (2013.01); *C12N 1/38* (2013.01); *C12P 1/04* (2013.01)

(58) Field of Classification Search
IPC ............ C12N 1/38; A23K 1/009; A23L 1/3014
See application file for complete search history.

(56) References Cited

FOREIGN PATENT DOCUMENTS

JP         2010057363 A  *  3/2010  ............... C12N 1/16

OTHER PUBLICATIONS

English translation of Ko, JP 2010-057363 A.*
Colorless Sulfur Bacteria, Hopkins Microbiology Course, 2010, web.stanford.edu/class/cee274s/.../CSB_BP.ppt, printed from the Internet on Nov. 21, 2014.*

* cited by examiner

*Primary Examiner* — Rosanne Kosson
(74) *Attorney, Agent, or Firm* — Hovey Williams LLP

(57) ABSTRACT

The present invention is directed to compositions and methods using microorganisms to benefit an environment or recipient subject. The present invention relates to the use of microorganism based compositions and methods to enhance the health of recipient subjects, improve soil conditions, and accelerate biodegradation. The present invention also relates to controlling insect and pest populations. Further, the present invention relates to the replacement of chemical compositions with microorganism based compositions.

35 Claims, 20 Drawing Sheets
(8 of 20 Drawing Sheet(s) Filed in Color)

LIQUID MICROORGANISM CONSORTIA FORMULATION

FIELD OF THE INVENTION

The present invention relates to microorganism compositions and methods of using. In particular, the present invention relates to a microorganism consortia composition including lactic acid, sulfide-utilizing, probiotic, and phototrophic microorganisms co-cultured to produce a composition useful in numerous industries including agriculture, food, health, and as a chemical replacement.

BACKGROUND OF THE INVENTION

Environmental awareness, resource constraints, and general public opinion are increasing the demand for efficient green technologies and products. Such green technologies and products are those that promote sustainability and have minimal impact on the environment. One area that is being exploited to develop green technology and products is the use of microorganisms and their specialized properties. Microorganisms have been used in agriculture, animal health, human health, and waste management. In agriculture, microorganisms are used to enhance composting and soil amendment. In animals and humans beneficial bacteria, known as probiotics, are used to prevent illness caused by harmful bacteria invading the natural flora. In waste management, microorganisms are used to accelerate waste decomposition and degrade odorous compounds.

While the use of microorganisms is being exploited, such use is hindered by stability, storage, and efficiency issues. Accordingly, there is a need to develop microorganism-based technologies and products that are stable under various conditions, have an appreciable shelf life, and can be easily used.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The following drawings form part of the present specification and are included to further demonstrate certain aspects of the present invention. The invention may be better understood by reference to one or more of these drawings in combination with the detailed description of specific embodiments presented herein.

SUMMARY OF THE INVENTION

Figure 1:
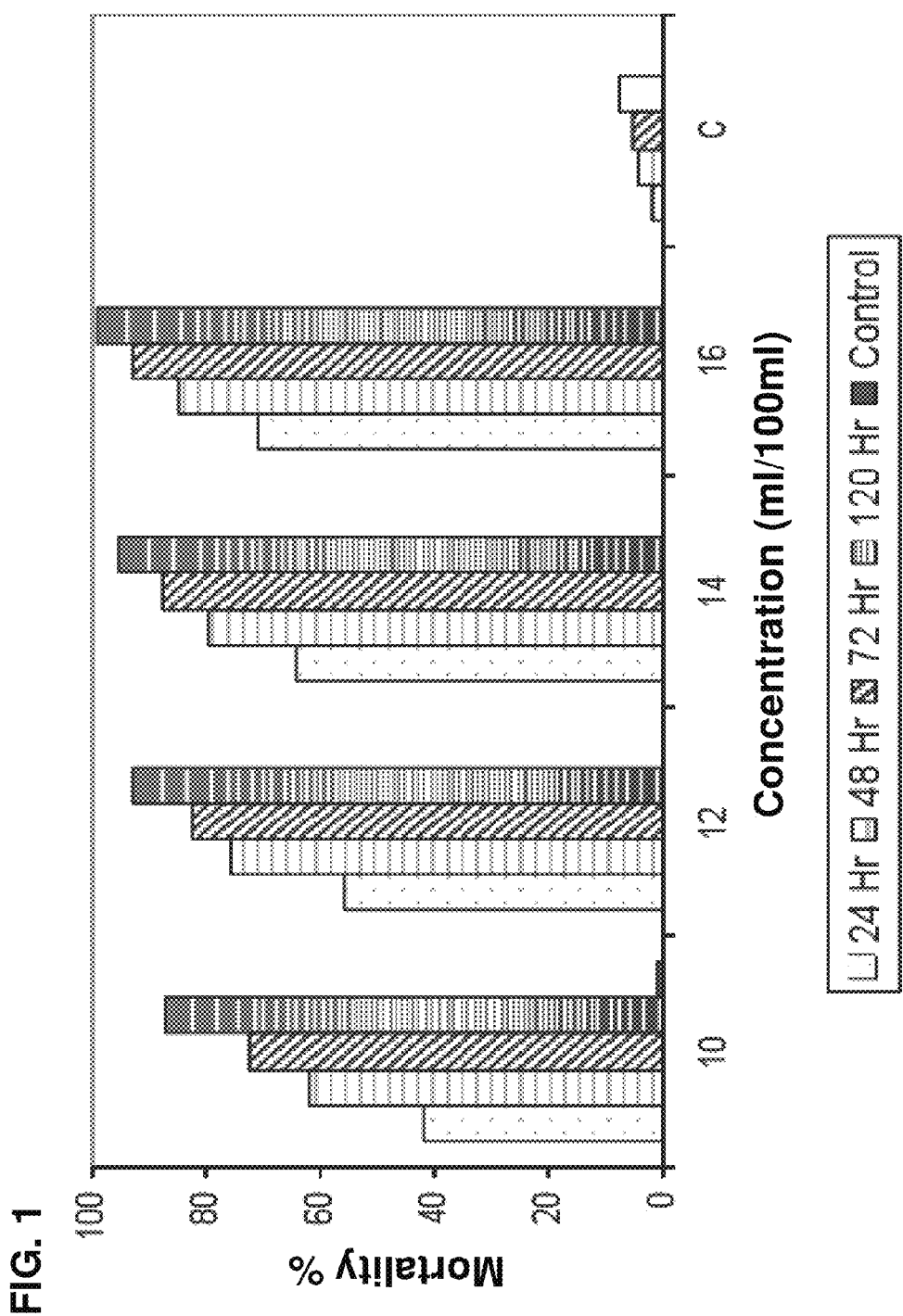
FIG. 1 graphically illustrates the effectiveness of different concentrations of a vector control formulation against *Culex quinquefasciatus* larvae following 24, 48, 72, and 120 hours of exposure.

The present invention is directed to compositions containing and methods using microorganisms. In particular, the present invention is directed to a composition containing at least 3 microorganisms. At least one microorganism is a sulfide-utilizing microorganism. Additional microorganisms include lactic acid, probiotic, and phototrophic microorganisms, as well as microorganisms having a nucleic acid sequence with at least 90% identity to SEQ ID NO: 1 and mixtures thereof. Microorganisms may be bacteria, yeast, fungi, or mold species or mixtures thereof.

In one embodiment, a composition includes at least one species of microorganism from lactic acid, probiotic, phototrophic, and sulfide-utilizing microorganism species. In another embodiment, the included sulfide-utilizing microorganism is a purple non-sulfur bacteria species. In another embodiment, the sulfide-utilizing microorganism has a nucleic acid sequence with at least 90% identity to SEQ ID NO: 1.

The compositions of the present invention may include additives. Such additives may support growth of microorganisms, induce production of specific metabolites by microorganisms, enhance the stability of the composition, add flavoring or color, add nutritive value, and provide other attributes to the compositions of the invention. Suitable additives include a carbon source, a nitrogen source, minerals, vitamins, alcohol, salts, acids, and other additives known in the art to support growth, induce specific metabolite production, add flavoring or color, or stabilize the composition.

In one embodiment, the carbon source includes molasses. In another embodiment, the composition includes minerals. Suitable minerals include magnesium, iron, phosphorus, potassium, and mixtures thereof. Suitable amounts of minerals include about 0.01% to about 10%. Preferably, the amount of minerals includes about 0.05% to about 3%. More preferably, the amount of minerals includes about 0.1% to about 2%. Most preferably, the amount of minerals includes about 0.3%

In another embodiment, the composition includes alcohol. Suitable amounts of alcohol include about 0.001% to about 20% w/v. Preferably, the amount of alcohol includes about 0.01 to about 10% w/v. More preferably, the amount of alcohol includes about 0.1% to about 8% w/v. Most preferably, the amount of alcohol includes about 5%.

In another embodiment, the composition includes acetic acid. Suitable amounts of acetic acid include about 0.001% to about 20% w/v. Preferably, the amount of acetic acid includes about 0.01 to about 10% w/v. More preferably, the amount of acetic acid includes about 0.1% to about 8% w/v. Most preferably, the amount of acetic acid includes about 5%.

In another embodiment, the composition includes salt, organic salts, molybdenum, sea kelp, or mixtures thereof. Suitable amounts of salt, molybdenum, and sea kelp include about 0.001% to about 5%. Any sea kelp known in the art may be used including, without limitation, kelp of the *Laminaria*, *Nereocystis*, and *Macrocystis* genras. Exemplary sea kelps include, *Laminaria digitata*, *L. hyperborean*, *L. ochroleuca*, *L. saccharina*, *L. agardhii*, *L. angustata*, *L. bongardina*, *L. cuneifolia*, *L. dentigera*, *L. ephemera*, *L. farlowii*, *L. groenlandica*, *L. japonica*, *L. longicruris*, *L. nigripes*, *L. ontermedia*, *L. pallida*, *L. platymeris*, *L. setchellii*, *L. sinclairii*, *L. solidungula*, *L. stenophylla*, *Alaria marginata*, *Costaria costata*, *Durvillea Antarctica*, *Durvillea willana*, *Durvillea potatorum*, *Ecklonia brevipes*, *Ecklonia maxima*, *Ecklonia radiate*, *Eisena arborea*, *Egregia menziesii*, *Hedophyllum sessile*, *Macrocystis angustifolia*, *Pleurophycus gardneri*, *Pterygophora californica*, *Saccharina japonica*, *Nereocystis luetkeana*, *Macrocystis pyrifera*, and others known in the art or yet to be discovered.

Preferably, the amount of salt, molybdenum, and sea kelp includes about 0.01% to about 1%. More preferably, the amount of salt, molybdenum, and sea kelp includes about 0.1% to about 0.5%. Most preferably, the amount of salt includes about 0.3%. Most preferably, the amount of molybdenum or sea kelp includes about 0.01%.

In another embodiment, the composition includes water. Suitable amounts of water include about 1% to about 99% of weight/volume (w/v). Preferably, the amount of water is about 30% to about 99% w/v. More preferably, the amount of water is about 40% to about 95% w/v. Most preferably, the amount of water is about 70% w/v.

The compositions of the invention may be in aqueous or dry form.

The composition may be provided in a diluted or concentrated form. In one embodiment, the composition is concentrated. In another embodiment, the composition is diluted.

The compositions of the invention may be used for insect control, health supplementation, chemical replacement, soil enrichment, plant enrichment, biodegradation enhancement, food fermentation, and in cleaning solutions.

Methods of the present invention include administering a microorganism composition of the invention to a subject. In one aspect, the composition is orally administered to a subject. In another aspect, the composition is added to food or liquid to be ingested by the subject. The composition may be sprayed on food, in water, or directly in the oral cavity of a subject.

Methods of the present invention include using a microorganism composition of the invention in agriculture practices. In one aspect, the composition is used to enrich soil. The composition may be applied to the soil in liquid or dry form. Further, fertilizer or other additives may be applied with the composition to the soil. The composition may be applied to the soil surface or mixed into the soil using methods known in the art, such as plowing. In another aspect, the composition may be used to enrich plants. The composition may be applied to soil or a water source of the plant in liquid or dry form. Further, fertilizer or other additives may be applied with the composition to the soil or water source of the plant. In another aspect, the composition may be used to preserve cut flowers or plants. The composition may be applied to the soil or water the cut flowers or plants are preserved in. In another aspect, the composition may be used to enrich seeds prior to planting. The seed may be soaked in an aqueous solution containing the composition.

Methods of the present invention include using a microorganism composition as a chemical replacement. In one aspect, the composition is used as an insecticide or pesticide to increase insect or pest mortality. The composition may be applied to an area in liquid or dry form. Such areas include outside and inside areas as well as directly to the skin of subjects.

Methods of the invention also include using microorganism compositions as cleaning solutions. The composition may be applied to any washable surface or to water. In one aspect, the composition is applied to a body of water such as a pool, pond, lake, lagoon, river, or aquarium. In another aspect, the composition is applied to a hard surface such as concrete, wood, synthetic material, plastic, tile, linoleum, vinyl, fiberglass, composite, glass, granite, marble, or metal. In another aspect, the composition is applied to waste holding containers such as lagoons, septic tanks, drain pipes, lateral lines, holding tanks, cesspools, and drain fields.

Methods of the invention also include using microorganism compositions in food products made using fermentation. The composition may be applied during the food production process in place of or in conjunction with fermentation agents typically used. The composition may be used in the production of any food requiring fermentation. Examples include, without limitation, beer, wine, cheese, milk, yogurt, kimchi, cider, bread, sauerkraut, sausages, vinegar, pickled foods, alcohol, olives, oilseed, chocolate, vanilla, hot sauce, pepperoni, salami, and other foods known in the art or yet to be discovered that rely on fermentation.

DETAILED DESCRIPTION

In accordance with the present invention, compositions including multiple microorganisms as well as methods of use have been discovered. In particular, it has been discovered that a consortium of microorganisms can be cultured to produce compositions having enhanced stability and shelf-life. Such compositions are useful in the agriculture, food, and health industries, as well as chemical replacement in other industries.

I. Compositions

Compositions useful in this invention include microorganisms and additives. The microorganisms may include species of bacteria and fungi, including yeast and mold species. Suitable microorganisms include those commonly known in the art as phototrophic, lactic acid, probiotic, and sulfide-utilizing microorganisms.

Examples of useful phototrophic, lactic acid, probiotic, and sulfide-utilizing microorganisms are found, for example, in Bergey's Manual of Determinative Bacteriology and Bergey's Manual of Systematic Bacteriology. For example, sulfide-utilizing microorganisms include species of Purple Non-sulfur Bacteria, Chromatianeae, Green Sulfur Bacteria, Colorless Sulfur Bacteria, and Filamentous Green Bacteria. Probiotic microorganisms may include *Lactobacillus* genus, *Enterococcus* genus, *Bifidiobacterium* genus, *Bacillus* genus, *Pseudomonas* genus, *Sporolactobacillus* genus, *Micromonospora* genus, *Micrococcus* genus, *Rhodococcus* genus, and *E. coli*. Phototrophic microorganisms may include *Rhodopseudomonas*, *Rodobactor*, and combinations thereof. For example, phototrophic microorganisms may include *Rhodopseudomonas palustris*, *R. sphaeroides*, *Rhodospirillum centenum*, *R. photometricum*, *R. rubrum*, *Rhodopila globiformis*, *Rhodobacter sphaeroides*, and combinations thereof. Lactic acid microorganisms may include *Lactobacillus*, *Lactococcus* and combinations thereof. For examples, lactic acid microorganisms may include *Lactobacillus casei*, *L. plantarum*, *L. acidophilus*, *L. fermentum*, *L. brevis*, *L. lactis*, *L. reuteri*, *L. bulgaricus*, *L. cellobiosus*, *L. curvatus*, *L. delbrukil*, *L. helbeticus*, *L. euterii*, *L. salivarius*, *L. rhamnosus*, *L. gaserli*, *L. jensenii*, *L. sporogenes*, *Lactococcus lactis*, *Streptococcus* (*Enterococcus*) *faecium*, *S. faecalis*, *S. cremoris*, *S. diacetylactis*, *S. intermedius*, *S. lactis*, *S. thermophilus*, *Pediococuss acidilactici*, *P. cerevisiae* (*damnosus*), *P. pentosaceus*, *P. acidilacticii*, *Leuconostoc mesenteroides*, and combinations thereof. Bacilli microorganisms may include *Bacillus* genus and combinations thereof. For example, Bacilli microorganisms may include *Bacillus licheniformis*, *B. subtilus*, *B. toyoi*, *B. amyloliquefaciens*, *B. megateriu*, *B. pumilus*, *B. coagulans*, *B. lentus*, *B. thermophilus*, *B. laterosporus*, *B. cereus*, *B. circulans*, and combinations thereof. *Bifidobacterium* microorganisms may include *Bifidobacterium* genus and combinations thereof. For example, *Bifidobacterium* microorganisms may include *Bifidobacterium bifidum*, *B. pseudolongum*, *B. thermophilus*, *B. adolescentis*, *B. animalis*, *B. infantis*, *B. longum*, and combinations thereof. *Pseudomonas* microorganism may include *Pseudomonas aeruginosa*, *P. putida*, *P. cepacia*, *P. fluorescens*, and combinations thereof. Yeast microorganisms may include *Saccharomyces* genus and combinations thereof.

In another aspect, the invention includes at least one microorganism encoding SEQ ID NO: 1 or a nucleic acid sequence at least about 45%, preferably 55%, 65%, 75%, 85%, 95%, or 99% identical to SEQ ID NO: 1.

To determine the percent identity of two nucleic acids, the sequences are aligned for optimal comparison purposes (e.g., gaps can be introduced in the sequence of a first nucleic acid sequence for optimal alignment with a second nucleic acid sequence). The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences (i.e., % identity=# of identical positions/total # of positions.times.100).

The determination of percent homology between two sequences may be accomplished using a mathematical algorithm. A preferred, non-limiting example of a mathematical algorithm utilized for the comparison of two sequences is the algorithm of Karlin and Altschul (1990) Proc. Nat'l Acad. Sci. USA 87:2264-2268, modified as in Karlin and Altschul (1993) Proc. Nat'l Acad. Sci. USA 90:5873-5877. Such an algorithm is incorporated into the NBLAST and XBLAST programs of Altschul, et al. (1990) J. Mol. Biol. 215:403-410. BLAST nucleotide searches can be performed with the NBLAST program, score=100, wordlength=12 to obtain nucleotide sequences similar or homologous to nucleic acid molecules of the invention. To obtain gapped alignments for comparison purposes, Gapped BLAST can be utilized as described in Altschul et al. (1997) Nucleic Acids Res. 25:3389-3402. When utilizing BLAST and Gapped BLAST programs, the default parameters of the respective programs (e.g., XBLAST and NBLAST) can be used.

Preferably, at least one microorganism is included in the compositions of the invention. More preferably, the compositions include consortiums of two or more microorganisms. It is contemplated that where two or more microorganisms form the composition, the microorganisms are co-cultured. The microorganisms may be propagated by methods known in the art. For example, the microorganisms may be propagated in a liquid medium under anaerobic or aerobic conditions. Suitable liquid mediums used for growing microorganism include those known in the art.

In one aspect, the composition includes a total number of microorganisms of about 1 to about 1 million colony forming units (CFU) per milliliter. Preferably, the composition includes a total number of microorganisms of about 100,000 to about 800,000 CFU per milliliter. More preferably, the composition includes a total number of microorganisms of about 250,000 to about 600,000 CFU per milliliter. Most preferably, the composition includes a total number of microorganisms of about 300,000 CFU per milliliter.

In one aspect, the composition includes living and non-living microorganisms. In another aspect, the composition includes living or non-living microorganisms. Compositions containing non-living microorganisms may contain extracts of the microorganisms. Such extracts may be considered a liquid fermentation product of the living microorganisms. The extracts of microorganisms include, by way of example, enzymes, metabolites, proteins, and other substances that are produced by microorganisms and are capable of eliciting an effect on an environment regardless of the living status of the microorganism.

In one aspect, the composition is fermented to produce a fermentation product. The composition may be fermented for about 1, 2, 3, 4, 5, 6, 7, 8, 9, 10, 11, 12, 13, 14, 15, 16, 17, 18, 19, 20, 21, 22, 23, 24, 25, or more days. Preferably, the composition is fermented for at least about 15 to about 23 days. More preferably, the composition is fermented for at least 21 days.

The compositions may also include additives. Suitable additives include substances known in the art that may support growth, production of specific metabolites by the microorganism, alter pH, enrich for target metabolites, enhance insecticidal effects, and combinations thereof. Exemplary additives include carbon sources, nitrogen sources, inorganic salt, organic acid, growth media, vitamins, minerals, acetic acid, amino acids and the like.

Examples of suitable carbon sources include, without limitation, starch, peptone, yeast extract, amino acids, sugars such as glucose, arabinose, mannose, glucosamine, maltose, sugar cane, molasses, rum, and the like; salts of organic acids such as acetic acid, fumaric acid, adipic acid, propionic acid, citric acid, gluconic acid, malic acid, pyruvic acid, malonic acid and the like; alcohols such as ethanol, glycerol, and the like; oil or fat such as soybean oil, rice bran oil, olive oil, corn oil, and sesame oil. The amount of the carbon source added varies according to the kind of carbon source and is typically between 1 to 100 grams per liter of medium. The weight fraction of the carbon source in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition. Preferably, molasses is contained in the medium as a major carbon source, at a concentration of about 2 to 20% (w/v). More preferably, the molasses is at a concentration of about 8 to 12% (w/v).

Examples of suitable nitrogen sources include, without limitation, amino acids, yeast extract, tryptone, beef extract, peptone, potassium nitrate, ammonium nitrate, ammonium chloride, ammonium sulfate, ammonium phosphate, ammonia or combinations thereof. The amount of nitrogen source varies according to the nitrogen source, typically between 0.1 to 30 grams per liter of medium. The weight fraction of the nitrogen source in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

Examples of suitable inorganic salts include, without limitation, potassium dihydrogen phosphate, dipotassium hydrogen phosphate, disodium hydrogen phosphate, magnesium sulfate, magnesium chloride, ferric sulfate, ferrous sulfate, ferric chloride, ferrous chloride, manganous sulfate, manganous chloride, zinc sulfate, zinc chloride, cupric sulfate, calcium chloride, sodium chloride, calcium carbonate, sodium carbonate, and combinations thereof. The weight fraction of the inorganic salt in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

In one embodiment, the compositions of the present invention may further comprise alcohol. Suitable alcohols include any known in the art including, without limitation, methanol, ethanol, n-propanol, allyl alcohol, n-propanol, isopropanol, sec-propanol, n-butanol, sec-butanol, isobutanol, t-butanol, and tert-amyl-alcohol. The weight fraction of the alcohol in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

In another embodiment, the compositions of the present invention may further comprise acetic acid or carboxylic acid. Suitable acetic acids include any known in the art including, without limitation, formic acid, acetic acid, propionic acid, butanoic acid, isobutyric acid, 3-methyl butanoic acid, methyl acetate ethyl acetate, propyl acetate, butyl acetate, isobutyl acetate, and 2-methyl butyl acetate. In one embodiment, the acetic acid is included by using vinegar. The weight fraction of the acetic acid in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

In yet another embodiment, the compositions of the present invention may further comprise any insect repellents known in the art. Such insect repellants include, without limitation, N,N-diethyl-m-toluamide (DEET), N,N-diethyl-benzamide, menthyl 2-pyrrolidone-5-carboxylate, N-aryl and N-cycloalkyl neo-alkanamides, N-lower alkyl neoalkanamides, nepetalactone and combinations thereof. The compositions may also comprise natural oils known for their insect repellent characteristics. Such natural oils include, without limitation, citronella oil, catnip oil, eucalyptus oil, cypress oil, galbanum oil, tolu, Peru balsams, and combinations thereof. The weight fraction of the insect repellents in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The compositions of the invention may be in liquid or dry form. The composition may comprise an aqueous suspension of components. This aqueous suspension may be provided as a concentrated stock solution which is diluted prior to application or as a diluted solution ready-to-use. Also, the composition may be a wettable powder, granules, dust, pellet or colloidal concentrate. Such dry forms may be formulated to dissolve immediately upon wetting or dissolve in a controlled-release, sustained-release, or other time-dependent manner. Also, the composition may be in a dry form that does not depend upon wetting or dissolving to be effective.

The compositions may additionally be provided in a formulation capable of spray. The spray may be a liquid or an aerosol.

The compositions of the present invention may also be formulated in a nutritional composition (e.g. foodstuff, food additive, dietary supplement, or feed additive). For example, the compositions may be included in food products made using fermentation techniques such as wine, beer, and cheese.

A nutritional composition of the present invention may include any of a variety of nutritional agents, which are well known in the art, including vitamins, minerals, essential and non-essential amino acids, carbohydrates, lipids, foodstuffs, dietary supplements, and the like. Thus, the compositions of the present invention may include fiber, enzymes and other nutrients. Preferred fibers include, but are not limited to: psyllium, rice bran, oat bran, corn bran, wheat bran, fruit fiber and the like. Dietary or supplementary enzymes such as lactase, amylase, glucanase, catalase and the like can also be included. Vitamins for use in the compositions of the present invention include vitamins B, C, D, E, folic acid, K, niacin, and the like. Typical vitamins are those, recommended for daily consumption and in the recommended daily amount (RDA).

The compositions of the present invention may be formulated in a pharmaceutical composition, where it is mixed with a pharmaceutically acceptable carrier for any type of administration route, selected according to the intended use.

In some embodiments, the combination of the invention may comprise at least one optional excipient. Non-limiting examples of suitable excipients include antioxidants, additives, diluents, binders, fillers, buffering agents, mineral salts, pH modifying agents, disintegrants, dispersing agents, flavoring agents, nutritive agents, oncotic and osmotic agents, stabilizers, preservatives, palatability enhancers and coloring agents. The amount and types of excipients utilized to form the combination may be selected according to known principles of pharmaceutical science.

In one embodiment, the excipient may include at least one diluent. Non-limiting examples of suitable diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lacitol, mannitol, malitol, sorbitol, xylitol, maltodextrin, and trehalose.

In another embodiment, the excipient may comprise a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof.

In another embodiment, the excipient may include a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may comprise a buffering agent. Representative examples of suitable buffering agents include, but are not limited to, MOPS, HEPES, TAPS, Bicine, Tricine, TES, PIPES, MES, Tris buffers or buffered saline salts (e.g., Tris buffered saline or phosphate buffered saline).

In a further embodiment, the excipient may include a disintegrant. Suitable disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth.

In yet another embodiment, the excipient may include a dispersion enhancer. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In a further embodiment, the excipient may include a lubricant. Non-limiting examples of suitable lubricants include minerals such as talc or silica; and fats such as vegetable stearin, magnesium stearate or stearic acid.

In still another embodiment, it may be desirable to provide a coloring agent. Suitable color additives include, but are not limited to, food, drug and cosmetic colors (FD&C), drug and cosmetic colors (D&C), or external drug and cosmetic colors (Ext. D&C).

The weight fraction of the excipient(s) in the combination may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the combination.

The compositions of the present invention are stable under various conditions as a liquid or dry form. Preferably, the compositions of the present invention are stable at room temperature.

II. Methods

The compositions disclosed herein are useful in agriculture, human and animal health, food, and as chemical replacements. The present invention encompasses methods of benefiting an environment or subject that would benefit from a microorganism composition. The methods may be used to replace chemical compositions, such as insecticides, pesticides, or chemicals. The methods may be used to benefit an environment, such as controlling insect populations, enhancing soil for agriculture purposes, and reducing odor associated with waste. Also, the methods may be used to support or enhance health in a subject. The methods may be used to treat a subject harboring a condition that would benefit from microorganism based therapy or that is at risk of developing a condition that would benefit from microorganism based therapy.

Agriculture

The compositions disclosed herein are useful in agriculture methods. Methods of the invention include soil enrichment, plant enrichment, and enhancing biodegradation.

Methods of soil enrichment include applying the composition to the soil to be enriched. The composition may be in liquid or dry form and applied to the soil by methods known in the art. Exemplary methods include spraying, dropping, scattering, and dusting the target soil. Also, the composition may be applied to a water source that feeds the target soil.

In another aspect, the composition may be used for plant enrichment. Methods of plant enrichment include applying the compositions of the invention to the soil or water source of the plant as described herein. Also, the composition may be added to the water of cut flowers or plants. In another aspect, seeds may be soaked in a composition of the invention prior to planting. It will be recognized that it may be beneficial to combine any of the methods described herein for soil and plant enrichment.

Addition of a microorganism composition has the effect of enhancing biodegradation of various wastes. Such wastes include, without limitation, food waste, waste produced by humans or animals, and landfill waste. A microorganism composition also has the effect of enhancing composting.

The microorganism composition may be provided either dried or in liquid form to a waste product. The microorganism composition may be provided in a variety of amounts with respect to the weight of the waste product depending on the waste product. In some aspects, the microorganism composition is provided in an amount ranging from about 0.5 to 50 wt % of the total weight of the waste product. In another aspect, the microorganism composition is provided in an amount ranging from about 1 to about 3 wt % of the total weight of the waste product. In another aspect, the amount of microorganism composition provided to the waste is about 2 wt % of the total amount of waste.

The microorganism may be provided in either dry form, liquid form or through the spray. Methods of treating waste products include without limitation, spraying, dusting, sprinkling, liquid inoculation, misting, fumigating, aerosolizing, and other methods known in the art.

Health

Methods of the invention include administering compositions to recipient subjects to support and promote health. Methods of the invention include administering compositions to recipient subjects to treat conditions including gastrointestinal and extraintestinal conditions.

Examples of gastrointestinal conditions include, without limitation, acute diarrhea, traveler's diarrhea, lactose intolerance, HIV-associated diarrhea, sucrose isomaltase deficiency, inflammatory bowl disease, pouchitis, carcinogenesis, enteral feeding associated diarrhea, antibiotic associated diarrhea, small bowel bacterial overgrowth, irritable bowel syndrome and conditions associated with enteropathogens. Such enteropathogens include, without limitation, *Helicobacter pylori, Campylobacter jejuni, Campylobacter coli, Staphylococcus aureus, Staphylococcus epidermidis, Streptococcus pyogenes, Streptococcus pneumoniae, Enterococcus faecalis, Haemophilus influenzae, Escherichia coli, Klebsiella pneumoniae, Enterobacter cloacae, Citrobacter freundii, Serratia marcescens, Pseudomonas aeruginosa* and *Pseudomonas maltophilia, Salmonella* sp., *Gasterophilus* sp., *Habronema* sp., *Crascia* sp., *Trichostrongvlus* sp., *Parascaris* sp., *Stroncrulus* sp., *Triodontophorus* sp., *Oxvuris* sp., *Stroncivloides* sp., *Anonlocephala* sp., *Paranonlocephala* sp., *Haemonchus* sp., *Hvostroncmulus* sp., *Spirocerca* sp., *Physoloptera* sp., viruses such as rotavirus, fungi such as *Candida albicans* and *Aspergillus fumigatus*, other species known or found to be associated with gastrointestinal conditions, and combinations of these species. Also contemplated are pathogens known in the art to cause gastrointestinal conditions such as those described in "Merck's Veterinary Manual" by Cynthia M. Kahn or "The Merck Manual of Diagnosis and Therapy" by Mark H. Beers, both incorporated herein by reference.

Also contemplated, is the use of microorganism compositions to treat extraintestinal conditions. Without being bound to a theory, extraintestinal conditions may be treated with microorganisms, microorganism extracts, or microorganism products that can stimulate multiple defense mechanisms including promotion of a nonimmunologic gut defense barrier. This barrier may inhibit translocation of potential pathogens and thus prevent infections of the blood stream and other tissues or organs. Another defense mechanism includes enhancing the intestine's immunologic barrier.

Examples of extraintestinal conditions include, without limitation, appendicitis, autoimmune disorders, multiple sclerosis, Alzheimer's disease, rheumatoid arthritis, celiac disease, diabetes mellitus, organ transplantation, periodontal disease, urogenital diseases (vaginal, urethral and perineal), sexually transmitted disease, HIV infection, HIV replication, surgical associated trauma, surgical-induced metastatic disease, sepsis, weight loss, anorexia, fever control, cachexia, wound healing, ulcers, gut barrier function, allergy, asthma, respiratory disorders, rhinovirus-associated diseases, otitis media, sinusitis, pulmonary disease, circulatory disorders, coronary heart disease, anemia, disorders of the blood coagulation system, renal disease, disorders of the central nervous system, hepatic diseases, constipation, ischaemia, nutritional disorders, osteoporosis, endocrine disorder, epidermal disorders, psoriasis, anthrax, and acne, as well as other conditions known in the art or yet to be discovered that may benefit from treatment with microorganisms, microorganism extracts, or microorganism products.

In use, the microorganism composition may be implemented in a number of different ways depending in part on the targeted subjects and goal of application. A liquid solution containing a microorganism composition may simply be applied directly in the subject's mouth or onto food or beverage the subject will consume. For example, an exemplary liquid spray formulation containing a microorganism composition may be sprayed, for example, on the subject's food prior to consumption.

It should be understood that the microorganism mixture used may be provided in the form of pure concentrate (100% concentration) or a diluted composition with additional excipients in the dosage form (i.e. the amount of active ingredient in the composition is less than or equal to 99.99%, and the remainder consists of inactive excipients). If diluted, the amount of microorganism composition dispensed in the various dosage forms may range from about 1 to 30%, more preferably between about 4 to 8%. One of skill in the art will appreciate that the volume of active component added to the composition will need to be adjusted to account for the dilution and to ensure the end composition comprises the appropriate final concentration of microorganism composition. One of skill in the art will also appreciate that the various components of the composition may be provided in a variety of dosage forms including, but not limited to liquid solution or suspension, emulsion, aerosol, slow release matrices, and the like.

Typical concentration range of microorganisms administered is $10^3$ to $10^{13}$ cells per day. Preferably, at least about $10^6$, at least about $10^7$, at least about $10^8$ cells per day are administered. However, it will be appreciated that the amount of bacteria to be administered will vary according to a number of parameters including subject's size, type of disorder and severity of symptoms.

Food

Methods of the invention include using compositions in the preparation of foods that require fermentation. Suitable foods include those known in the art such as beer, wine, cider, dough-based products, breads, and dairy products. Also contemplated are methods using compositions for preservation techniques.

The microorganism composition can be provided to fermentable foods along with fermentation microorganisms. In some aspects, the microorganism composition may replace the microorganisms typically used in fermentation, in other aspects they add to the effect of the fermentation microorganisms.

The amount of microorganism composition added to the food product will vary depending on the food product, in some embodiments, the microorganism composition is provided as a dry powder and in other embodiments the microorganism composition is provided as a liquid. Dry formulations of the compositions may be from about 1% to about 99% or more by weight of the composition, while liquid formulations may generally comprise from about 1% to about 99% or more of the microorganism composition by weight.

Chemical Replacement

Methods of the invention include using compositions in place of chemicals. Because the compositions of the present invention are uniquely suited for use in a wide variety of chemical-replacement applications such as for insecticides, pesticides, and cleaning solutions, a wide variety of chemicals may be replaced by use of the invention and such replacements are incorporated therein.

1. Vector Control

The microorganism compositions disclosed herein are particularly useful as insecticides for topical or systemic application to an environment. Such environments include, without limitation, field crops, grasses, fruits and vegetables, lawns, trees, ornamental plants, sand, humans, animals, and other environments that may benefit from insecticide application. The compositions may be formulated for preventative or prophylactic application to an area, and may in certain circumstances be applied to pets, livestock, animal bedding, humans, or in and around farm equipment, barns, domiciles, agricultural facilities, industrial facilities, and other areas that would benefit from insecticide application.

The microorganism compositions are applied to an area or environment of the target insect by conventional methods. Such methods include, without limitation, spraying, dusting, sprinkling, soil soaking, soil injection, seed coating, seedling coating, foliar spraying, aerating, misting, atomizing, fumigating, aerosolizing, and other methods known in the art.

The microorganism compositions may be used in consecutive or simultaneous application to an environmental site alone or in combination with one or more additional insecticides, pesticides, chemicals, fertilizers, or other compounds. The compositions may also be used in conjunction with other treatments such as fertilizers, weed killers, cryoprotectants, surfactants, detergents, insecticidal soaps, dormant oils, polymers, time-release or biodegradable carrier formulations that permit long-term dosing of a target area following a single application of the formulation. Likewise, the formulations may be prepared into edible "baits" or fashioned into insect "traps" to permit feeding or ingestion by a target insect.

An insect as repelled by the composition of this invention includes any member of a large group of invertebrate animals characterized, in the adult state (non-adult insect states include larvae and pupae), by division of the body into head, thorax, and abdomen, three pairs of legs, and, often, but not always) two pairs of membranous wings. This definition therefore includes but is not limited to a variety of biting insects (e.g., ants, bees, black flies, chiggers, fleas, green head flies, mosquitoes, stable flies, ticks, wasps), wood-boring insects (e.g., termites), noxious insects (e.g., house flies, cockroaches, lice roaches, wood lice), and household pests (e.g., flour and bean beetles, dust mites, moths, silverfish, weevils). The compositions of the present invention are effective insect repellents against a wide spectra of common insect pests, such as those mentioned above and also including biting insects, wood-boring insects, noxious insects, and household pests, most particularly mosquitoes, sand flies, stable flies, and ticks. The invention also includes effectiveness against all stages of invertebrate animals including adult, larvae, and pupae stages.

Regardless of the method of application, the amount of the composition is applied at an insecticidally-effective amount, which will vary depending on such factors as, for example, the specific target insects to be controlled, the specific environment, location, plant, crop, or agricultural site to be treated, the environmental conditions, and the method, rate, concentration, stability, and quantity of application of the composition. The formulations may also vary with respect to climatic conditions, environmental considerations, frequency of application, and severity of insect infestation.

The concentration of insecticidal composition which is used for environmental, systemic, topical, or foliar application will vary widely depending upon the nature of the particular formulation, means of application, environmental conditions, and degree of activity. Typically, the insecticidal composition will be present in the applied formulation at a concentration of at least about 1% by weight and may be up to and including about 99% by weight. Dry formulations of the compositions may be from about 1% to about 99% or more by weight of the composition, while liquid formulations may generally comprise from about 1% to about 99% or more of the composition by weight. As such, a variety of formulations are preparable, including those formulations that comprise from about 5% to about 95% or more by weight of the composition mix, including those formulations that comprise from about 10% to about 90% or more by weight of the composition. Naturally, formulations may comprise from about 15% to about 85% or more by weight of the composition, and formulations comprising from about 20% to about 80% or more by weight of the composition are also considered to fall within the scope of the present disclosure.

In compositions in which intact microorganisms are included, preparations will generally contain from about $10^4$ to about $10^8$ cells/mg, although in certain embodiments it may be desirable to utilize formulations comprising from about $10^2$ to about $10^4$ cells/mg, or when more concentrated formulations are desired, compositions comprising from about $10^8$ to about $10^{10}$ or $10^{11}$ cells/mg may also be formulated.

The insecticidal formulation of the invention may be administered to a particular area or environment in one or more applications as needed, with a typical field application rate per hectare ranging on the order of from about 50 g/hectare to about 500 g/hectare of composition, or alternatively, from about 500 g/hectare to about 1000 g/hectare may be utilized. In certain instances, it may even be desirable to apply the composition to a target area at an application rate of from about 1000 g/hectare to about 5000 g/hectare or more of composition. In fact, all application rates in the range of from about 50 g of composition per hectare to about 10,000 g/hectare are contemplated to be useful in the management, control, and killing of target insect pests using such insecticidal formulations. As such, rates of about 100 g/hectare, about 200 g/hectare, about 300 g/hectare, about 400 g/hectare, about 500 g/hectare, about 600 g/hectare, about 700 g/hectare, about 800 g/hectare, about 900 g/hectare, about 1 kg/hectare, about 1.1 kg/hectare, about 1.2 kg/hectare, about 1.3 kg/hectare, about 1.4 kg/hectare, about 1.5 kg/hectare, about 1.6 kg/hectare, about 1.7 kg/hectare, about 1.8 kg/hectare, about 1.9 kg/hectare, about 2.0 kg/hectare, about 2.5 kg/hectare, about 3.0 kg/hectare, about 3.5 kg/hectare, about 4.0 kg/hectare, about 4.5 kg/hectare, about 6.0 kg/hectare, about 7.0 kg/hectare, about 8.0 kg/hectare, about 8.5 kg/hectare, about 9.0 kg/hectare, and even up to and including about 10.0 kg/hectare or greater of composition may be utilized in certain agricultural, industrial, and domestic applications of the insecticidal formulations described herein.

2. Cleaning Solutions

Cleaning solutions that use the compositions of the invention are contemplated. In particular, cleaning solutions that replace all or part of the chemical component typically included in cleaning solutions are contemplated. Methods of cleaning include contacting a surface to be cleansed with a composition of the invention. The methods of the invention may be used to control odor, control disease causing pathogens, and break down sludge, scum, dirt, grease, and grime. In another aspect, a composition of the invention may be added to water to clean the water of impurities. The compositions of the invention may be used in cleaning solutions used to clean a variety of surfaces. Such surfaces include all washable surfaces and all hard surfaces, including plastic, fiberglass, wood, concrete, synthetic materials, composite materials, vegetation, fruits, vegetables, and others known in the art. Cleaning solutions including compositions of the present invention may also be used to clean water (i.e. ponds, lakes, rivers, aquariums, pools, etc.), septic tanks, holding tanks, and lagoons.

DEFINITIONS

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

As used herein, "administering" is used in its broadest sense to mean contacting a subject, surface, liquid, or environment with a composition of the invention.

The term "co-culture" refers to a culture of microorganisms that includes at least two microorganism of the present invention, described herein.

The term "insecticidally-effective amount" refers to an amount of the composition that is able to bring about death to at least one insect, or to noticeably reduce insect growth, feeding, or normal physiological development. This amount will vary depending on such factors as, for example, the specific target insects to be controlled, the specific environment, location, plant, crop, or agricultural site to be treated, the environmental conditions, and the method, rate, concentration, stability, and quantity of application. The formulations may also vary with respect to climatic conditions, environmental considerations, frequency of application, and severity of insect infestation.

The phrase "fermentation product" refers to a mixture including at least one microorganism, expression products of the microorganism(s), substances produced by the microorganisms, and extracts of the microorganisms.

The phrase "finished product" refers to a mixture including a fermentation product. The finished product may include additional additives.

The term "pharmaceutical composition" refers to a preparation of one or more compositions of the invention with additional components such as physiologically suitable carriers and excipients. The purpose of a pharmaceutical composition is to facilitate administration of a composition to a recipient subject.

The term "physiologically acceptable carrier" refers to a carrier or a diluent that does not cause significant irritation to a subject and does not abrogate the biological activity and properties of the administered composition.

The term "excipient" refers to an inert substance added to a pharmaceutical composition to further facilitate administration of a composition. Examples, without limitation, of excipients include calcium carbonate, calcium phosphate, various sugars and types of starch, cellulaose derivatives, gelatin, vegetable oils and polyethylene glycols. Techniques for formulation and administration of pharmaceutical compositions are known in the art and may be found in "Remington's Pharmaceutical Sciences," Mack Publishing Co., Easton, Pa., latest edition, which is incorporated herein by reference.

As used herein, "subject" refers to a living organism having a central nervous system. In particular, subjects include, but are not limited to, human subjects or patients and companion animals. Exemplary companion animals may include domesticated mammals (e.g., dogs, cats, horses), mammals with significant commercial value (e.g., dairy cows, beef cattle, sporting animals), mammals with significant scientific values (e.g., captive or free specimens of endangered species), or mammals which otherwise have value. Suitable subjects also include: mice, rats, dogs, cats, ungulates such as cattle, swine, sheep, horses, and goats, lagomorphs such as rabbits and hares, other rodents, and primates such as monkeys, chimps, and apes. Subjects may be of any age including new born, adolescence, adult, middle age, or elderly.

As various changes could be made in the above compositions and methods without departing from the scope of the invention, it is intended that all matter contained in the above description and in the Examples given below, shall be interpreted as illustrative and not in a limiting sense.

EXAMPLES

Example 1

PNSB-Enhanced Microorganism Consortium Formulation

The PNSB-enhanced microorganism consortium formulations used in the Examples herein were made as follows according to Table 1. Purified water was added to a mixing tank. Molasses (Brix 80+5%, pH 5.7+0.5, Sucrose 30+5% or Total Sugar of 75+5%) was added to the water in the mixing tank. The water and molasses were mixed at 30 Hz speed and then SDA-3C, 199.9+0.1 Proof, 95+1% Ethanol, 4.75+0.50% IPA was added to the mix along with vinegar (120+1 Titratable Acidity). Next, mineral powder (0.15% Mg (as MgO), 0.6% Fe, 0.15% P (as $P_2O_5$), 3.2% K (as $K_2O$) was added to the mixture. The mixture was pumped into a fermentation tank. A probiotic mix (*Bacillus subtilis*, *Bifidobacterium animalis*, *Bifidobacterium bifidum*, *Bifidobacterium longum*, *Enterococcus lactis*, *Enterococcus thermophilus*, *Lactobacillus acidophilus*, *Lactobacillus bulgaricus*, *Lactobacillus casei*, *Lactobacillus fermentum*, *Lactobacillus plantarum*, *Rhodopseudomonas palustris*, *Rhodopseudomonas sphaeroides*, and *Saccharomyces cerevisiae*) was added into the mixing tank and blended. Then, the probiotic mix was pumped into the fermentation tank. The residue remaining in the mixing tank was rinsed using water and pumped into the fermentation tank. The probiotic mix was fermented for 21 days at a temperature of 38° C. and a pH below 3.6.

TABLE 1

| | Formulations | | | | | | | | |
|---|---|---|---|---|---|---|---|---|---|
| Water (L) | 3872.96 | 3567.2 | 2930 | 3908.8 | 2293.2 | 1019.2 | 3720.1 | 3337.9 | 2955.7 |
| Molasses (L) | 101.92 | 254.8 | 509.6 | 672 | 764.4 | 1019.2 | 101.92 | 101.92 | 101.92 |

TABLE 1-continued

| Formulations | | | | | | | | |
|---|---|---|---|---|---|---|---|---|
| Alcohol (L) | 509.6 | 764.4 | 1274 | 235.2 | 1783.6 | 2293.2 | 764.4 | 1274 | 1783.6 |
| Acetic Acid (L) | 611.52 | 509.6 | 382.2 | 280 | 254.8 | 764.4 | 509.6 | 382.2 | 254.8 |
| Mineral Powder (kg) | 25.48 | 10.19 | 5.1 | 16.8 | 2.55 | 38.22 | 10.13 | 5.1 | 25.48 |
| Probiotic Mix (kg) | 487.3 | 382.2 | 254.8 | 487.3 | 127.4 | 509.6 | 382.2 | 254.8 | 127.4 |

TABLE 2

| Formulations (Continued) | | | | | | | | |
|---|---|---|---|---|---|---|---|---|
| Water (L) | 1936.5 | 2802.8 | 2420.6 | 2038.4 | 2802.8 | 3465.3 | 3312.4 | 2420.6 | 2008.4 |
| Molasses (L) | 101.92 | 1019.2 | 1019.2 | 1019.2 | 1019.2 | 509.6 | 509.6 | 509.6 | 509.6 |
| Alcohol (L) | 2293.2 | 764.4 | 1274 | 1783.6 | 509.6 | 509.6 | 764.4 | 1783.6 | 2293.2 |
| Acetic Acid (L) | 764.4 | 509.6 | 382.2 | 254.8 | 764.4 | 611.52 | 509.6 | 382.2 | 254.8 |
| Mineral Powder (kg) | 38.22 | 10.2 | 5.1 | 25.48 | 38.22 | 25.48 | 25.48 | 25.48 | 25.48 |
| Probiotic Mix (kg) | 50.96 | 382.2 | 254.8 | 127.4 | 50.96 | 254.8 | 254.8 | 254.8 | 254.8 |

Example 2

Effectiveness of the PNSB-Enhanced Microorganism Consortium Formulation at Low Concentration on Insect Larvae The third instar larvae of various insect species were collected and exposed to different concentrations of PNSB-enhanced microorganism consortium formulation (Example 1). The larvae were exposed to 0.1%, 1.0%, and 3.0% concentrations of PNSB-enhanced microorganism consortium formulation diluted in water. The larvae were exposed for 24, 48, 72, 96, and 120 hours. As shown in Table 3, the PNSB-enhanced microorganism consortium formulation was effective against the third instar larvae of *Aedes* genus. The mortality rate increased with increasing concentrations of formulation and increasing exposure time.

TABLE 3

Bioassay data (% mortality) on the third instar larvae of *Aedes* genus exposed to various concentrations of PNSB-enhanced microorganism consortium formulation.

| Concentration | 24 hours | 48 hours | 72 hours | 96 hours | 120 hours |
|---|---|---|---|---|---|
| Control | Nil | Nil | Nil | Nil | Nil |
| 0.1% | Nil | 10% | 20% | 30% | 50% |
| 1.0% | Nil | 20% | 50% | 60% | 80% |
| 3.0% | 10% | 40% | 80% | 100% | 100% |

As shown in Table 4, the PNSB-enhanced microorganism consortium formulation was effective against the third instar larvae of *Culex* genus. The mortality rate increased with increasing concentrations of formulation and increasing exposure time.

TABLE 4

Bioassay data (% mortality) on the third instar larvae of *Culex* genus exposed to various concentrations of PNSB-enhanced microorganism consortium formulation.

| | 24 hours | 48 hours | 72 hours | 120 hours |
|---|---|---|---|---|
| Average mortality (%) | 89.20 | 97.10 | 96.27 | 99.17 |
| Control (%) | | | | 3.75 |

As shown in Table 5, the PNSB-enhanced microorganism consortium formulation was effective against the third instar larvae of wild *Culex* genus. The mortality rate increased with increasing concentrations of formulation and increasing exposure time.

TABLE 5

Bioassay data (% mortality) on the third instar larvae of wild *Culex* genus exposed to various concentrations of PNSB-enhanced microorganism consortium formulation.

| | 24 hours | 48 hours | 72 hours | 120 hours |
|---|---|---|---|---|
| Average mortality (%) | 18.80 | 38.80 | 61.30 | 82.50 |
| Control (%) | | | | 7.50 |

As shown in Table 6, the PNSB-enhanced microorganism consortium formulation was effective against the third instar larvae of *Anopheles* genus. The mortality rate increased with increasing concentrations of formulation and increasing exposure time.

TABLE 6

Bioassay data (% mortality) on the third stage larvae of *Anopheles* genus exposed to various concentrations of PNSB-enhanced microorganism consortium formulation.

|  | 24 hours | 48 hours | 72 hours | 120 hours |
|---|---|---|---|---|
| Average mortality (%) | 93.80 | 97.50 | 98.80 | 98.80 |
| Control (%) |  |  |  | 10.0 |

Example 3

Effectiveness of PNSB-Enhanced Microorganism Consortium Formulation at High Concentration on Insect Larvae The third instar larvae of *Aedes* and *Culex* genus were collected and exposed to various concentrations of PNSB-enhanced microorganism consortium formulation (Example 1). The larvae were exposed to 10%, 12%, 14% and 16% concentrations of formulation diluted in dechlorinated water. The larvae were exposed for 24, 48, 72, and 120 hours. As shown in FIG. 1, the formulation was effective against larvae of *Aedes* and *Culex* genus following 24, 48, 72, and 120 hours of exposure.

Example 4

Figure 2:
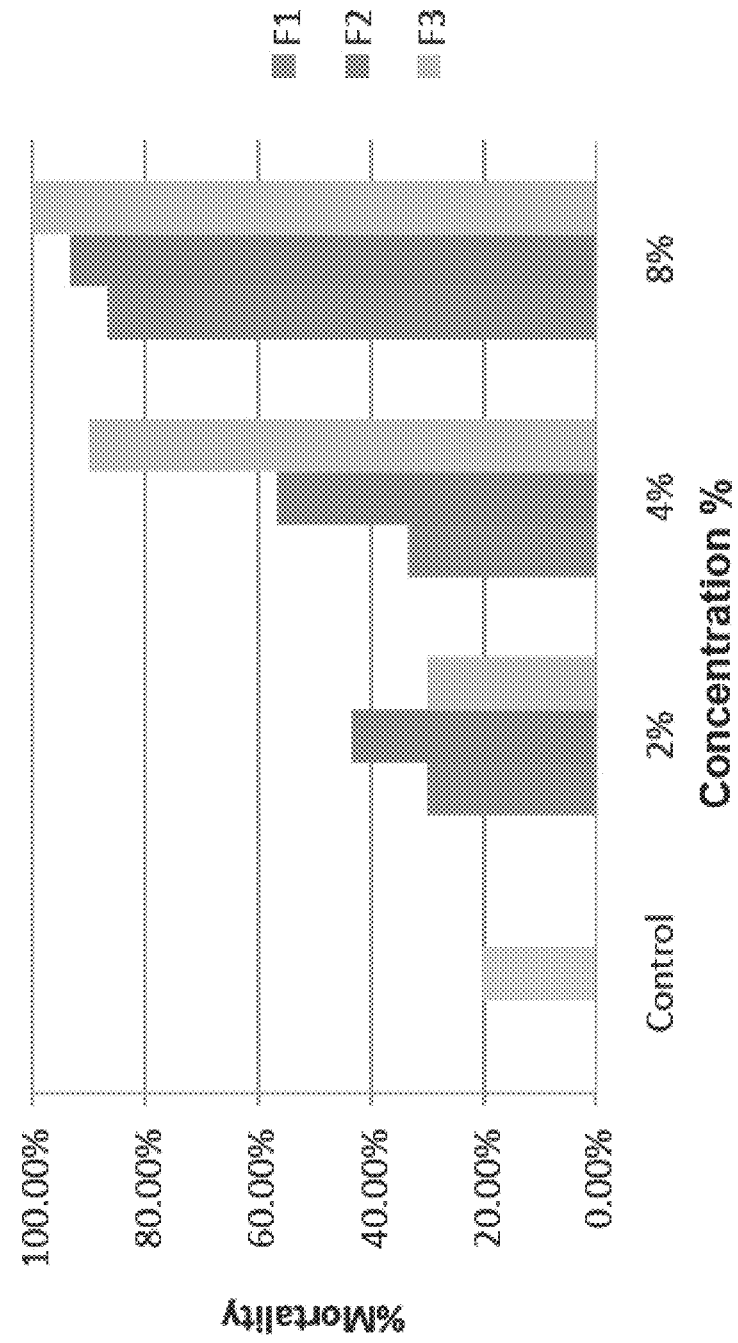
FIG. 2 graphically depicts the effectiveness of different vector control formulations (F1; F2; and F3) against *Culex* and *Aedes* species following 240 hours of exposure at 2%, 4%, and 8% concentrations.

Effectiveness of Various PNSB-Enhanced Microorganism Consortium Formulations on Insect Larvae The third instar larvae of *Aedes* and *Culex* species were collected and exposed to various concentrations of different formulations of PNSB-enhanced microorganism consortium formulation. The larvae were exposed to 2%, 4%, and 8% concentrations of formulation diluted in dechlorinated water. The larvae were exposed for 240 hours. Formulation F1 consisted of 72.17% water; 9.95% sugar; 3.48% isoproponol, 70% strength; 4.15% vinegar; 0.30% mineral powder; and 9.95% of PNSB enhanced microorganism consortium containing purple non-sulfur bacteria, chromatianeae, green sulfur bacteria, colorless sulfur bacteria, filamentous green bacteria, *Bacillus subtilis, Bifidobacterium animalis, Bifidobacterium bifidum, Bifidobacterium longum, Enterococcus lactis, Enterococcus thermophilus, Lactobacillus acidophilus, Lactobacillus bulgaricus, Lactobacillus casei, Lactobacillus fermentum, Lactobacillus plantarum, Rhodopseudomonas palustris, Rhodopseudomonas sphaeroides*, and *Saccharomyces cerevisiae*. Formulation F2 consisted of 69.8% water; 12% sugar; 4.2% alcohol; 5% vinegar; 0.3% mineral powder; and 8.7% PNSB enhanced microorganism consortium containing purple non-sulfur bacteria, chromatianeae, green sulfur bacteria, colorless sulfur bacteria, filamentous green bacteria, *Bacillus subtilis, Bifidobacterium animalis, Bifidobacterium bifidum, Bifidobacterium longum, Enterococcus lactis, Enterococcus thermophilus, Lactobacillus acidophilus, Lactobacillus bulgaricus, Lactobacillus casei, Lactobacillus fermentum, Lactobacillus plantarum, Rhodopseudomonas palustris, Rhodopseudomonas sphaeroides*, and *Saccharomyces cerevisiae*. Formulation F3 consisted of 87.29% water; 5% sugar; 0.3% salt; 0.3% mineral powder; and 7.11% PNSB enhanced consortium microorganisms containing purple non-sulfur bacteria, chromatianeae, green sulfur bacteria, colorless sulfur bacteria, filamentous green bacteria, *Bacillus subtilis, Bifidobacterium animalis, Bifidobacterium bifidum, Bifidobacterium longum, Enterococcus lactis, Enterococcus thermophilus, Lactobacillus acidophilus, Lactobacillus bulgaricus, Lactobacillus casei, Lactobacillus fermentum, Lactobacillus plantarum, Rhodopseudomonas palustris, Rhodopseudomonas sphaeroides*, and *Saccharomyces cerevisiae*. As shown in FIG. 2, the PNSB-enhanced microorganism consortium formulations were most effective against larvae at a concentration of 8%, regardless of the formulation. At a lower concentration of 4%, formula F3 was more effective than F2 and F1.

Example 5

Figure 3:
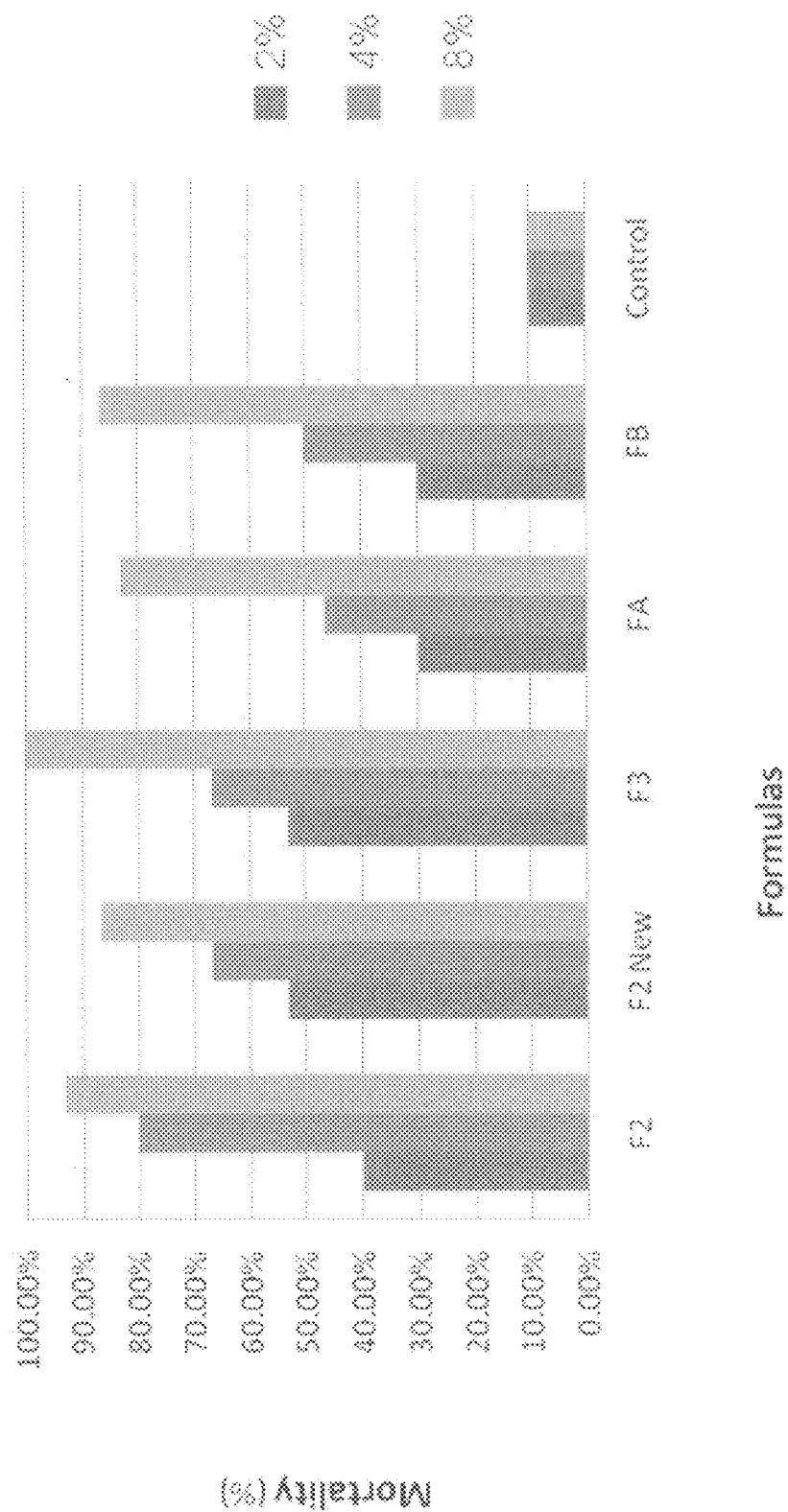
FIG. 3 graphically depicts the effectiveness of a vector control formulation at various concentrations (2%, 4%, and 8%) and different storage periods (F2: 8 months old; F2-new: 3 months old; F3: <1 month old) against killing mosquito larvae.

Effectiveness of PNSB-Enhanced Microorganism Consortium Formulation After Storage The third instar larvae of *Aedes* and *Culex* species were collected and exposed to different concentrations of PNSB-enhanced microorganism consortium formulation stored for various storage periods. The larvae were exposed to 2%, 4%, and 8% concentrations of formulation diluted in dechlorinated water. The larvae were exposed to formula F3 (Example 4) that was less than one month old, 8 months old (F2), or 3 months old (F2-New). The pH of the concentrated solutions was measured before dilution. The pH after 10 days (after larvae treatment) was also measured. The product pH ranges were from 3.29 to 3.95. As shown in FIG. 3, the formulations stored for 8 months remained effective against the larvae.

Example 6

Figure 4:
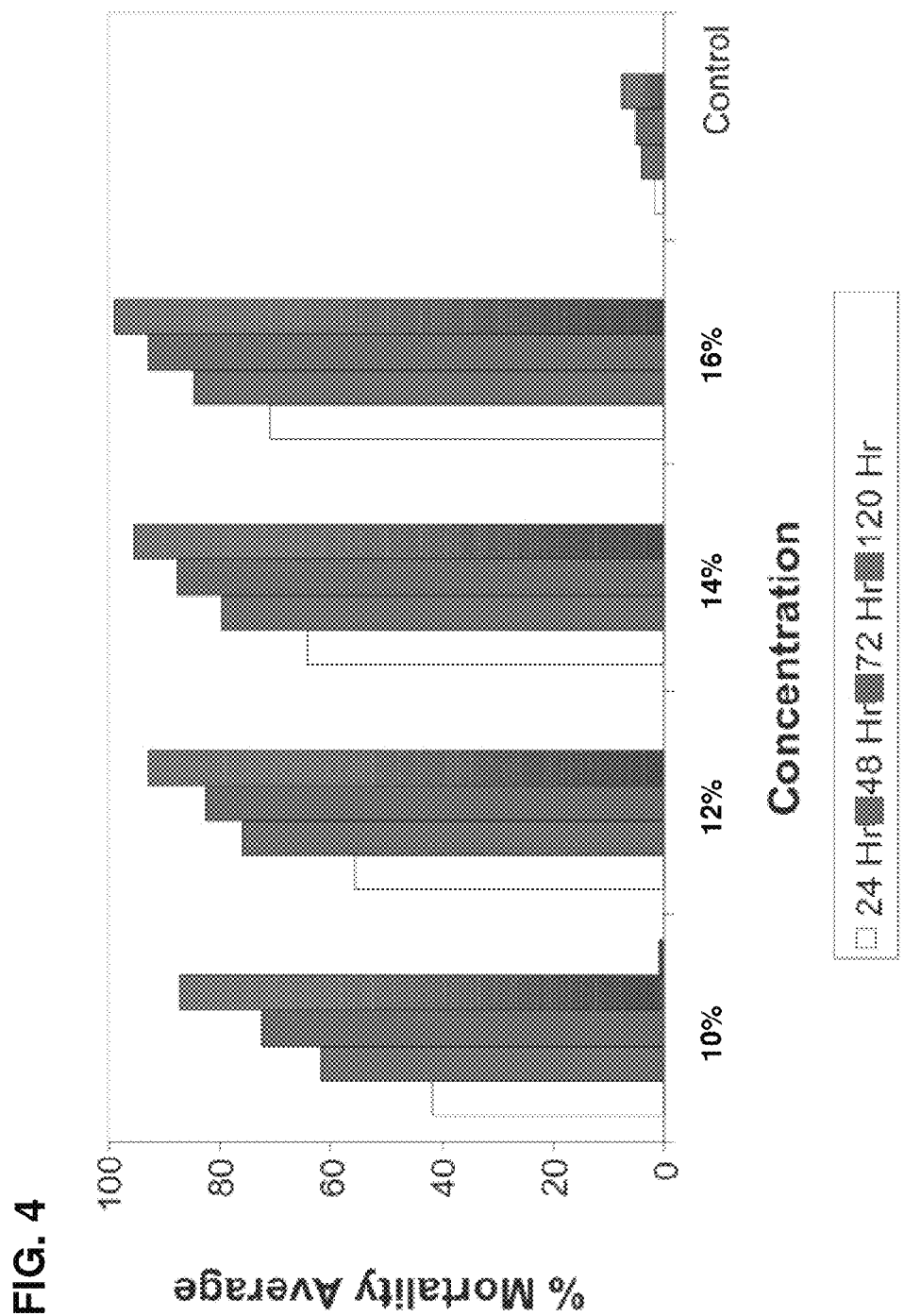
FIG. 4 graphically illustrates the average mortality rate of *Culex quinquefasciatus* mosquitoes over 120 hours in response to various concentrations of vector control formulation.

Effectiveness of PNSB-Enhanced Microorganism Consortium Formulation Against Mosquitoes and Sand Flies A location in Roatan, Honduras that included a beach, marina, and pool was used for a field test to analyze the effectiveness of PNSB-enhanced microorganism consortium formulation against pyrethroid-resistant insects. Laboratory tests were conducted to determine the appropriate application rate and protocol. *Culex quinqufasciatus* mosquitoes were exposed to different concentrations of formulation for 120 hours. These concentrations included 10%, 12%, 14%, and 16% of formulation. As shown in FIG. 4, the highest concentration of the formulation was the most effective against mosquitoes.

Figure 5:
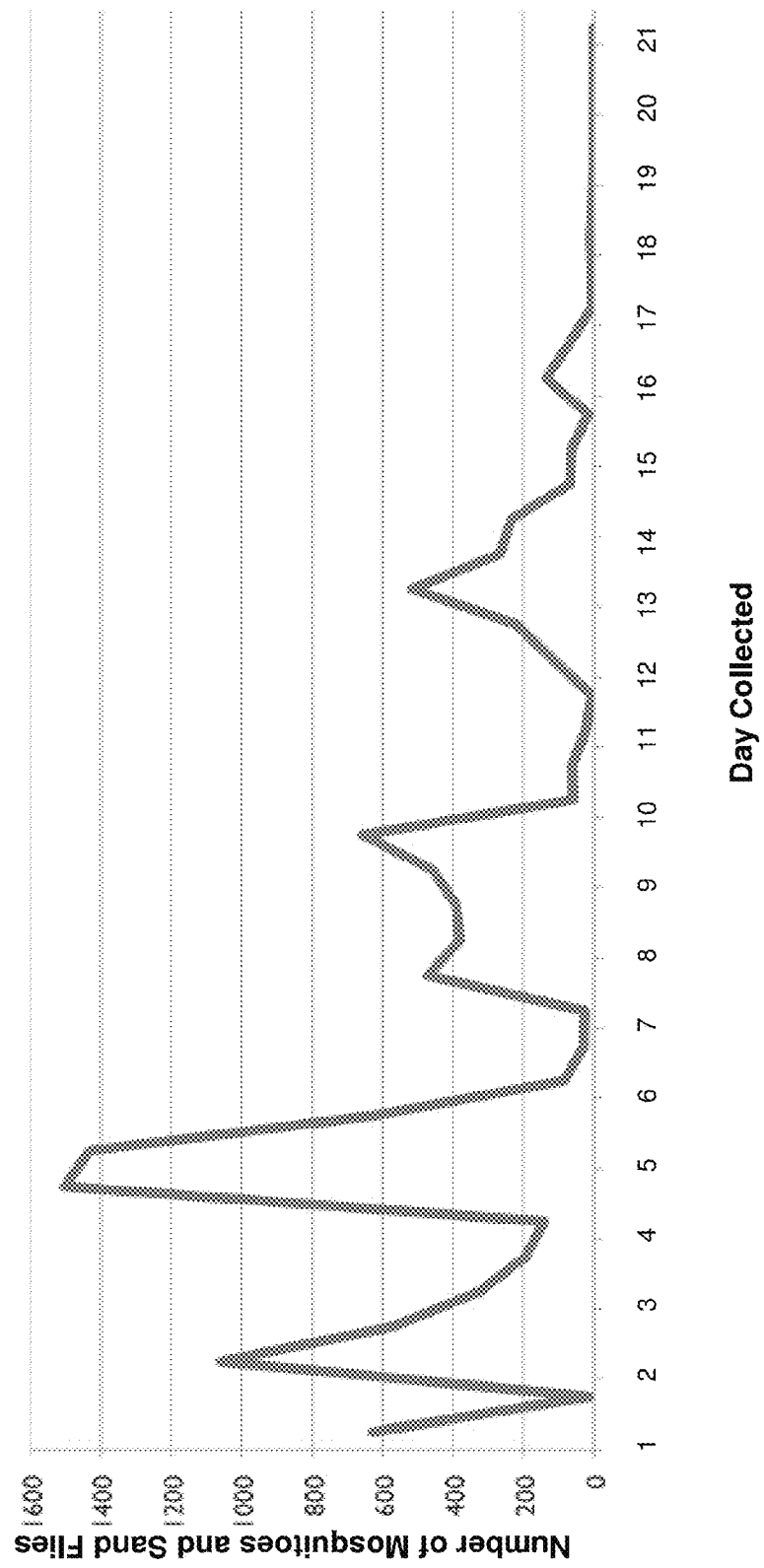
FIG. 5 graphically illustrates a decrease in the number of mosquitoes and sand flies collected each day during a 42 day field trial.

In a field study using the 12-15% concentration, the PNSB-enhanced microorganism consortium formulation was applied to areas where insects typically reproduce including sand and standing water. Approximately 4,300 liters were used over 18 acres throughout a 42 day trial period. Baseline samples were taken prior to the first treatment and no chemicals were used in the testing vicinity for four weeks prior. The formulation was applied daily for 42 days. Mosquito magnet machines were used to collect insects from marina, pool, and beach areas. The number of mosquitoes and sand flies collected were counted each day throughout the trial period. As shown in FIG. 5, there was a significant decrease in mosquitoes and sand flies in all areas where data was collected over the course of the field trial. In particular, there was a 99% reduction in mosquito larvae in standing water and pool areas. Also, there was a 94.3% reduction in sand flies.

Example 7

Microorganism Consortium Formulation for Plant and Seed Health

The PNSB-enhanced microorganism consortium formulations used in the Examples herein were made as described in Example 1.

Following fermentation, molybdenum is added to the fermentation product to make a formulation useful to enhance seed and plant growth and health. In particular, 0.01% by weight of molybdenum or sea kelp is added to the fermentation product.

Example 8

Microorganism Consortium Formulation Enhances Plant Health

Figure 6:
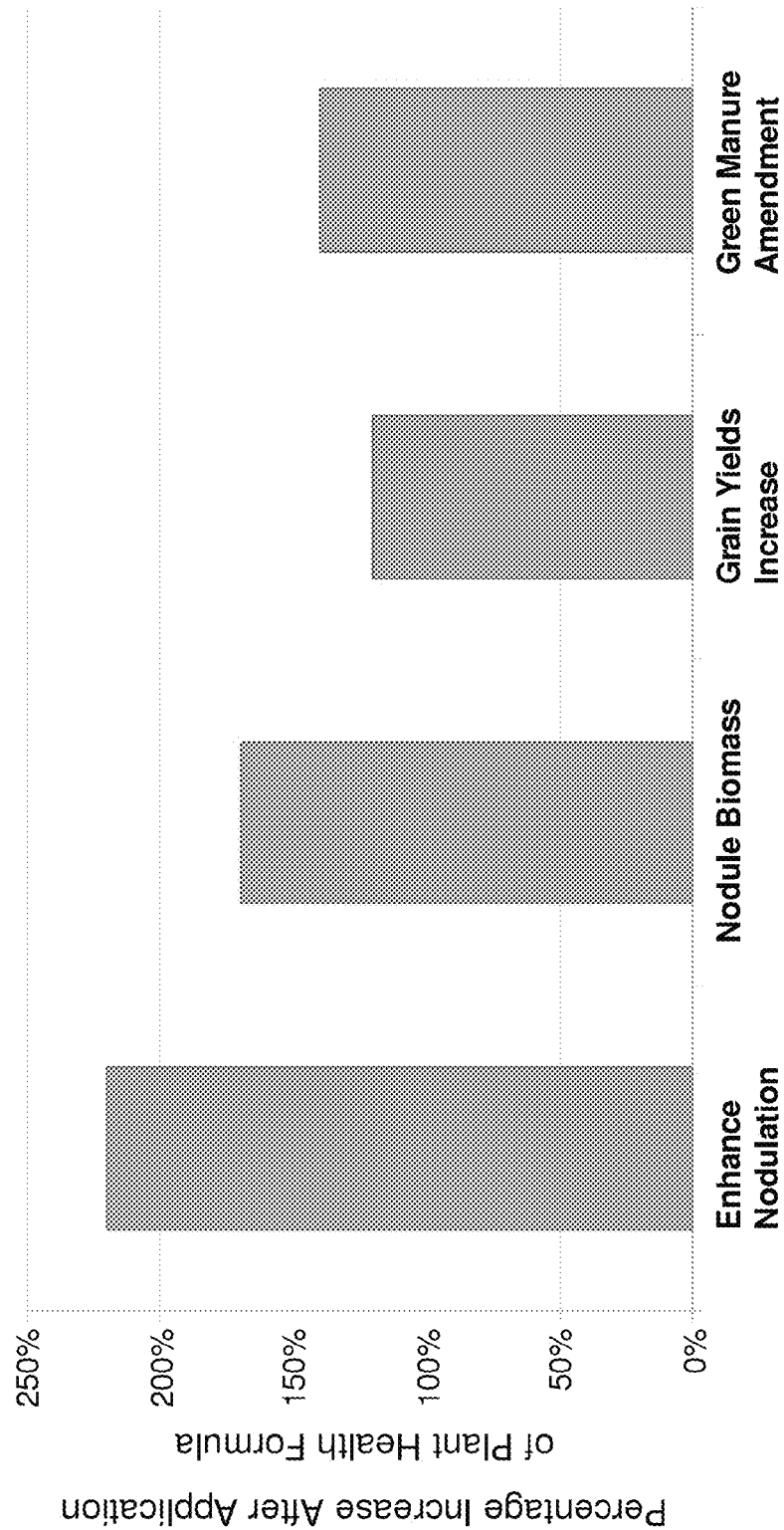
FIG. 6 graphically illustrates a percentage increase in plant nodulation, nodule biomass, grain yield and green manure amendment following application of the plant health formulation.
Figure 7:
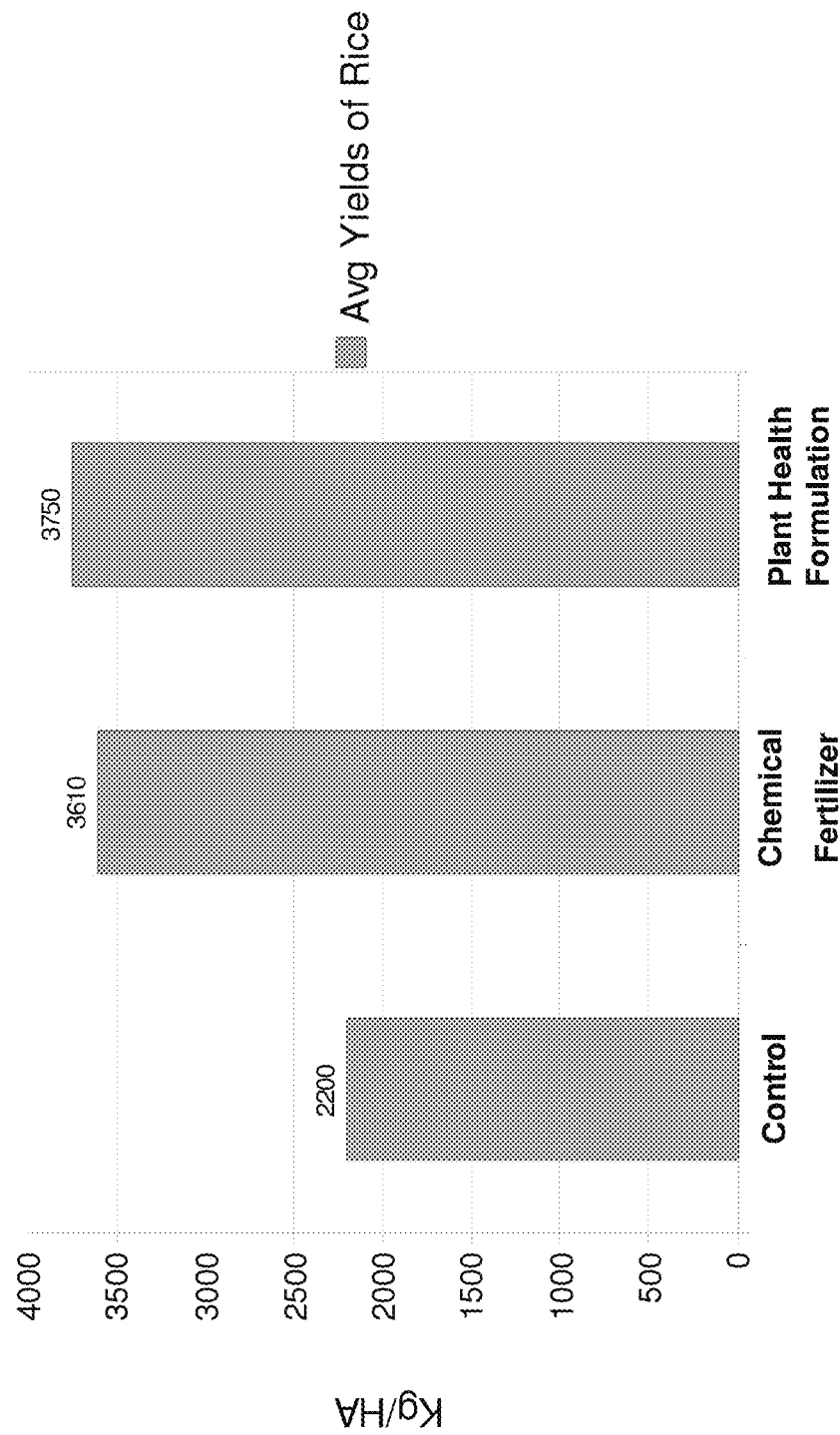
FIG. 7 graphically illustrates the average yield of rice of plants grown in untreated (control), biofertilizer (chemicals), or plant health formulation treated soil.
Figure 8:
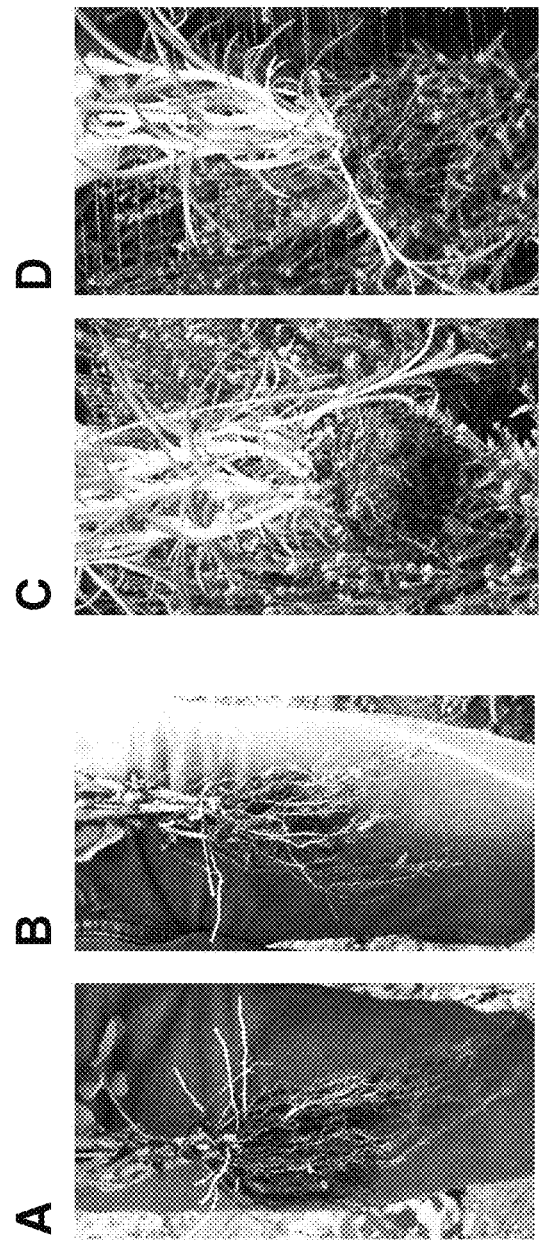
FIG. 8 shows pictures of plant roots grown in plant health formulation treated (FIGS. 8A and 8C) or untreated (FIGS. 8B and 8D) soil.

To analyze the effects of the formulation of Example 7 ("Plant Health Formulation") on plant and seed growth and health, the formulation was added to the soil or water used for growing various plants. In particular, tomato, pea, pepper, cucumber, beet, rice, and corn plants were grown in either soil treated with Plant Health Formulation, chemical fertilizer, or the soil was left untreated. These plants and the seeds thereof were compared with respect to seed germination, soil quality, foliar growth, and overall yield. The seeds grown in soil treated with the Plant Health Formulation had improved seed germination over seeds grown in soil treated with fertilizer or untreated soil (Table 7). The soil quality of the soil treated with the Plant Health Formulation had improved as provided in Table 8. In particular, the soil levels of nitrogen and potassium were enhanced (Table 9). Both foliar (FIG. 6) and root quality (FIG. 8) and growth were also increased in plants grown in soil treated with the Plant Health Formulation over fertilizer treated and untreated. Also, plants grown in soil treated with Plant Health Formulation and inoculated with *Xanthomonas campestris* pv *vesicatoria* exhibited a decrease in disease index compared to similarly treated plants grown in other soils (Table 10). Overall, rice plants grown in Plant Health Formulation treated soil demonstrated an increase in yield over plants grown in chemically treated or untreated soil (FIG. 7). In particular, there was a 71% increase over untreated soil.

TABLE 7

Seed Germination Percentage with Plant Health Formula.

| Crop | Plant Health Formula | Fertilizer | Control | Plant Health Formula Improvement over Fertilizer | Plant Health Formula Improvement over Control |
|---|---|---|---|---|---|
| Tomato | 66 | 46 | 6 | 43% | 1000% |
| Pea | 93 | 81 | 58 | 15% | 60% |
| Pepper | 67 | 42 | 16 | 60% | 319% |
| Cucumber | 87 | 82 | 62 | 6% | 40% |
| Beet | 146 | 92 | 83 | 59% | 76% |
| Corn | 94 | 79 | 72 | 19% | 31% |

TABLE 8

Soil Quality Improvement

| Soil Parameter | Before Plant Health Formula | After Plant Health Formula | % Improvement |
|---|---|---|---|
| Total Nitrogen as N % | 1.60 | 1.80 | 13% |
| Total Phosphorous as P % | 0.49 | 0.67 | 37% |
| Total Potassium as K % | 1.13 | 1.39 | 23% |
| Water Holding Capacity | 70 | 80 | 14% |
| Organic Matter % | 21 | 64 | 205% |
| Carbon: Nitrogen Ratio | 26:1 | 20:1 | 23% |
| *E. Coli* MPN/g | $11 \times 10^5$ | 400 | 99% reduction |

TABLE 9

Soil Quality Improvement Regarding Nitrogen and Potassium Levels.

| | Nitrogen | Potassium |
|---|---|---|
| Control | 1.5 | 2 |
| Plant Health Formula Treated | 4.4 | 2.7 |
| % Improvement | 193% | 35% |

TABLE 10

Effect of Plant Health Formulation on Disease Index.

| Treatment | Disease Index (%) |
|---|---|
| Plant Health Formula | 24.9 |
| Fertilizer | 33 |
| Fungicide | 28.8 |
| Control | 30.9 |

Example 9

PNSB-Enhanced Microorganism Consortium Formulation Used as Dog Food Supplement The PNSB-enhanced microorganism consortium formulation described in Example 1 may be used for the support of animal health ("Health Formulation"). In particular, the Health Formulation can be sprayed on food to be ingested by a dog.

Two trials were conducted using different amounts of the Health Formulation sprayed onto dog food. In the first trial, 2.75 mL of Health Formula was sprayed onto 400 grams of standard diet dog food and fed to 20 male and female Beagles. Over the course of a two day trial, 5.5 mL total of Health Formula was presented in the first trial. In the second trial, 5.5 mL of Health Formula was sprayed onto 400 grams of standard diet dog food and fed to 20 male and female Beagles. Over the course of a two day trial, 11.0 mL total of Health Formula was presented in the second trial.

For both trials, two stainless steel bowls were presented to each Beagle on an individual basis once daily for 2 days. One bowl contained food sprayed with the Health Formulation and the other bowl contained untreated food. Bowl placement was reversed daily and both bowls were presented for 30 minutes. If one food bowl was completely consumed prior to the end of the 30 minutes, both bowls were removed. Food consumption and first choice preference were recorded for each dog.

The statistics applied were the Wilcoxon test to establish non-parametric ranking of observed consumption differences and an Analysis of Variance in consumption. Individual t-tests were performed to determine the consumption preference of each dog. A Chi Square test was performed to establish the significance in first choice preference.

Figure 9:
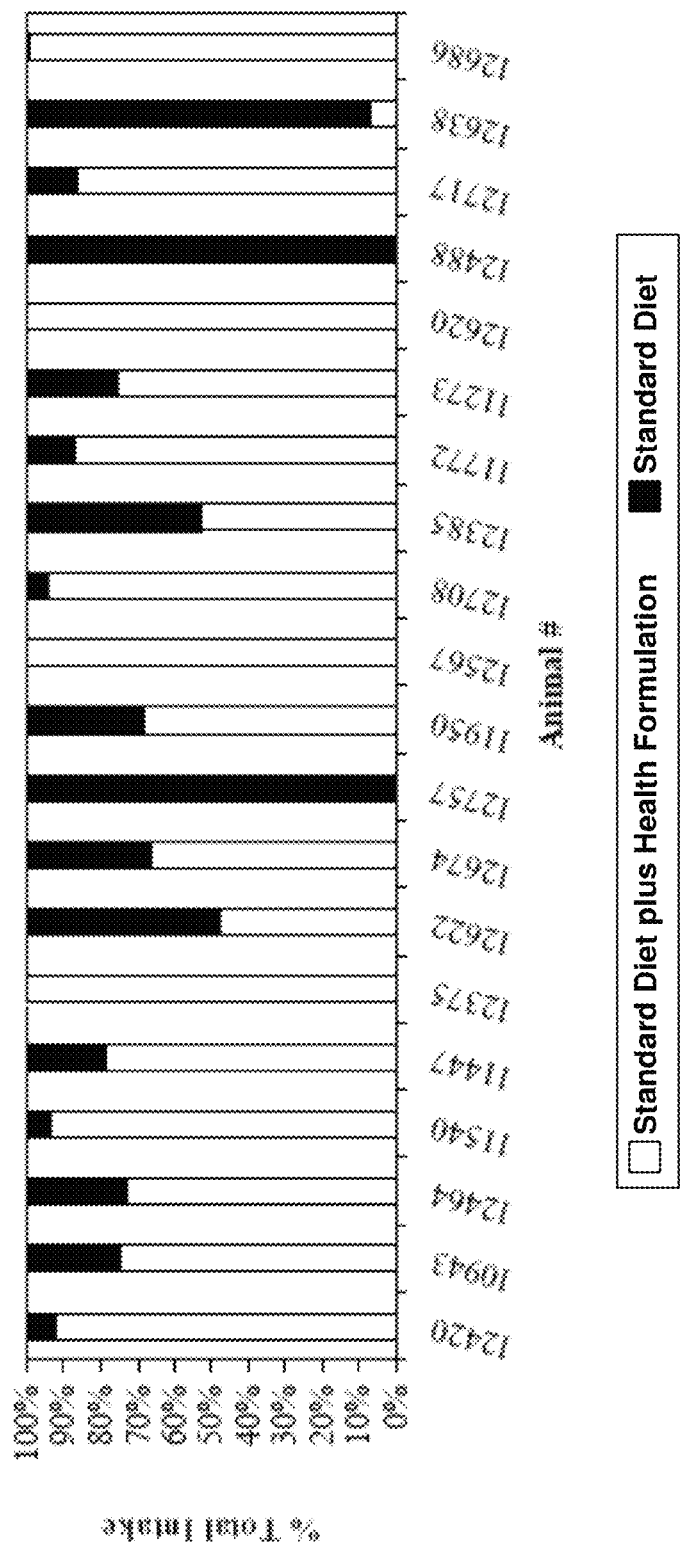
FIG. 9 graphically illustrates the percentage of Health Formulation treated (white) and untreated (black) food ingested by the test subjects.
Figure 10:
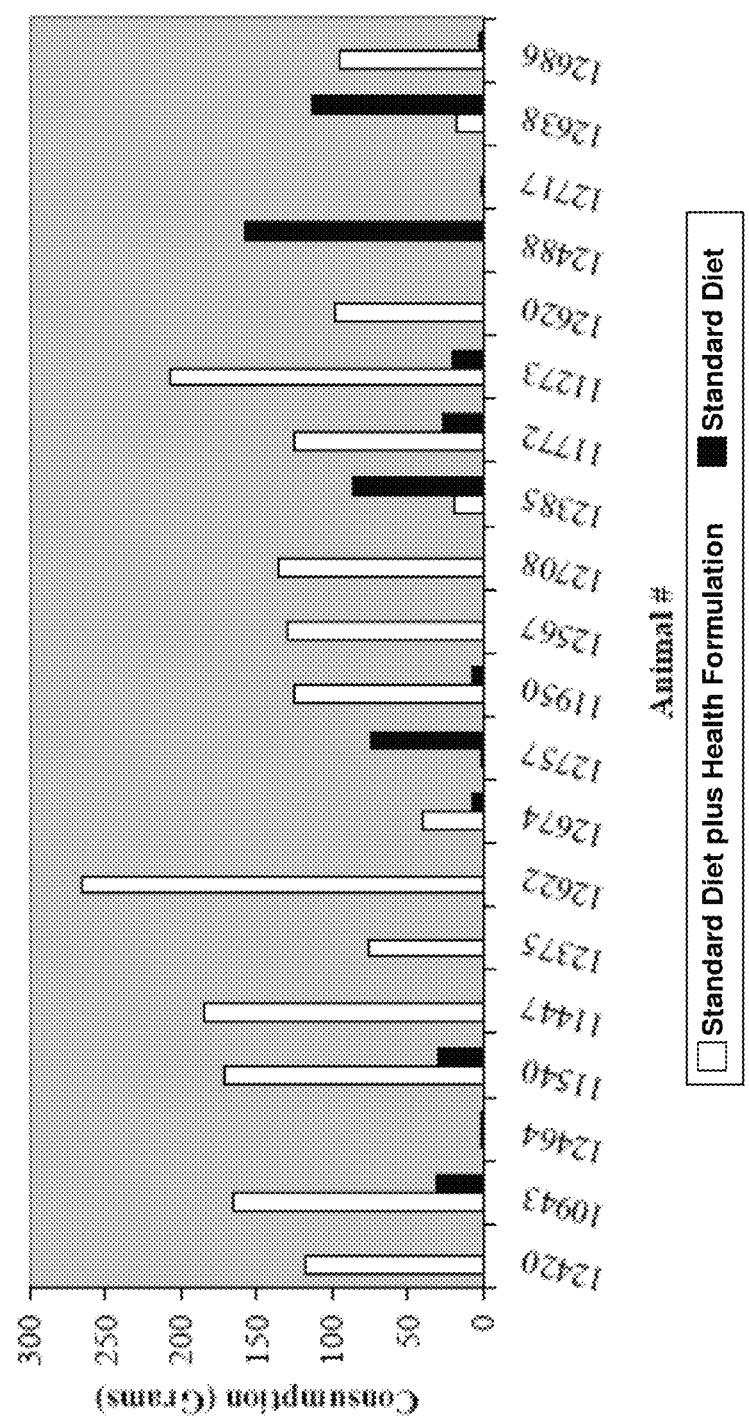
FIG. 10 graphically illustrates the amount of food consumed by the test subjects on day one of a two day study (treated, white; and untreated, black).
Figure 11:
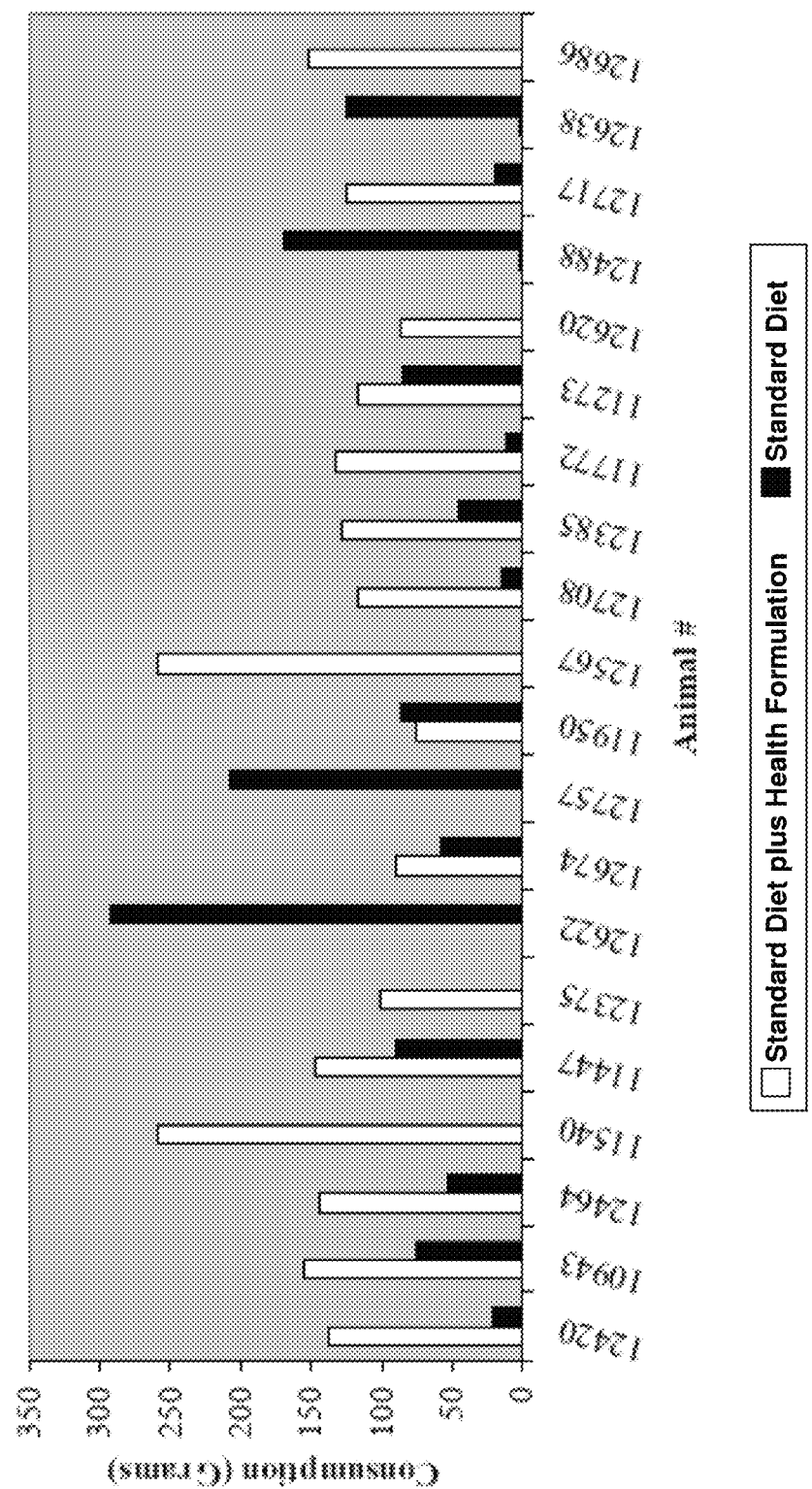
FIG. 11 graphically illustrates the amount of food consumed by the test subjects on day two of a two day study (treated, white; and untreated, black).
Figure 12:
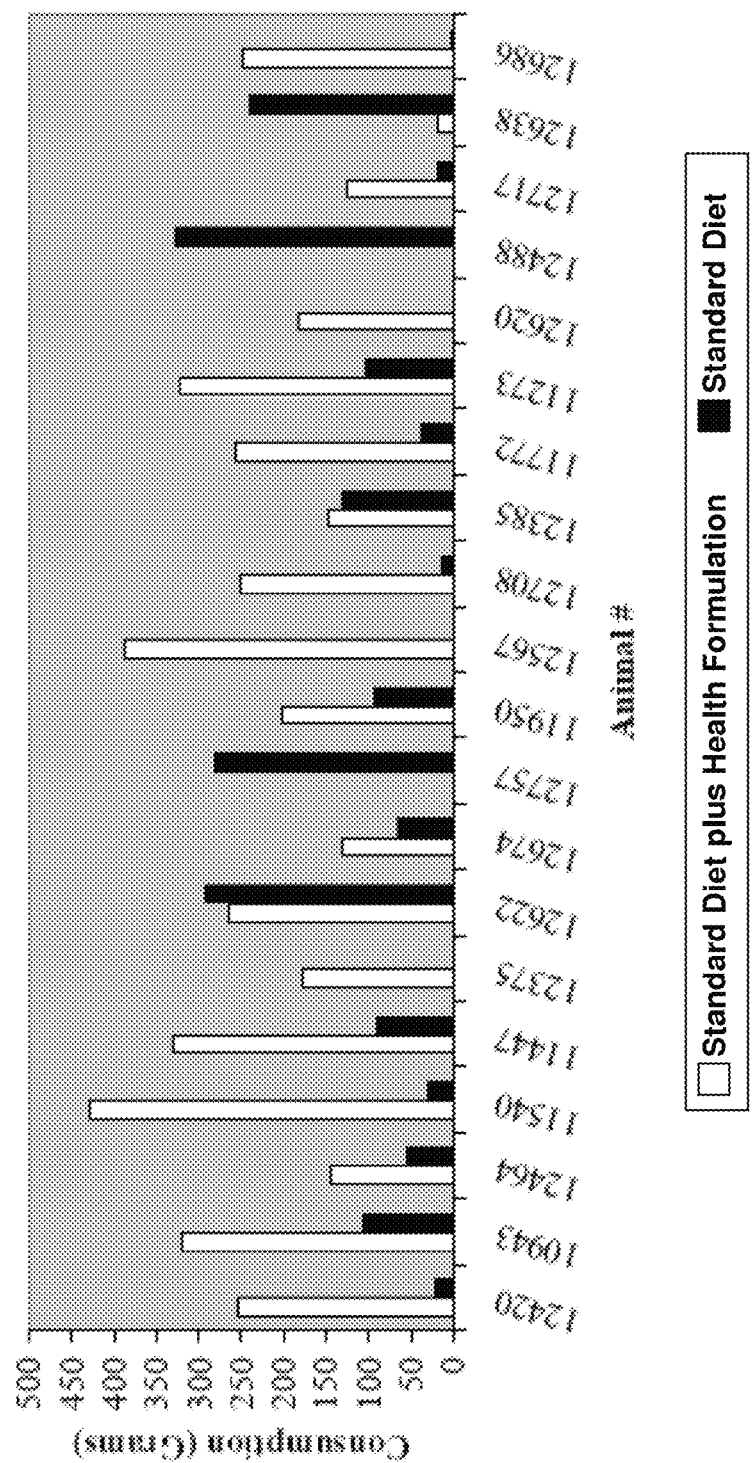
FIG. 12 graphically illustrates the total consumption of food by the test subjects over a two day study (treated, white; and untreated, black).

In the first trial, the total consumption of 20 dogs over two days was 4200 grams of the treated food (69%) and 1912 grams of the untreated food (31%). The individual consumption percentages for each dog in the trial are provided in FIG. 9. The individual consumption amounts of each food offered are provided in FIG. 10 for day 1 and FIG. 11 for day 2. Overall, the treated food was consumed 2.20 times more than the untreated food. The consumption preference included 3 dogs preferring the treated food (15%), 1 dog preferring the untreated food (5%), and 16 dogs having no preference (80%). In regards to the first choice preference, treated food was chosen first 36 times and untreated food 3 times. Overall, the treated food was a first choice 12 times more than the untreated food. As an individual choice, 17 dogs chose the treated food first (85%), zero dogs chose the untreated food first (0%), and 3 dogs had no preference (15%). Of the total food consumed, the average intake ratio of each diet was 70% of the treated food and 30% of the untreated food. The average individual consumption amounts over both days are provided in FIG. 12.

Figure 13:
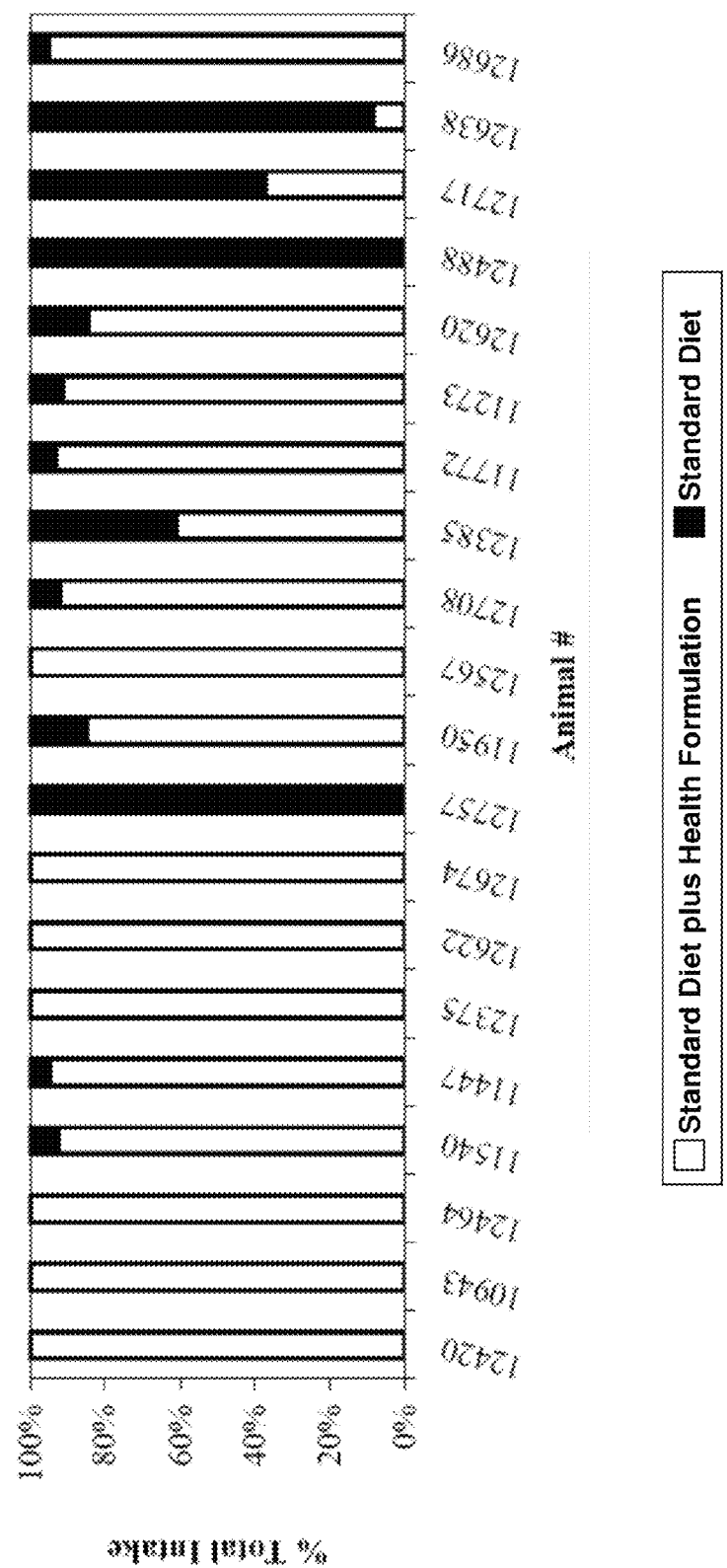
FIG. 13 graphically illustrates the percentage of treated (white) and untreated (black) food ingested by the test subjects.
Figure 14:
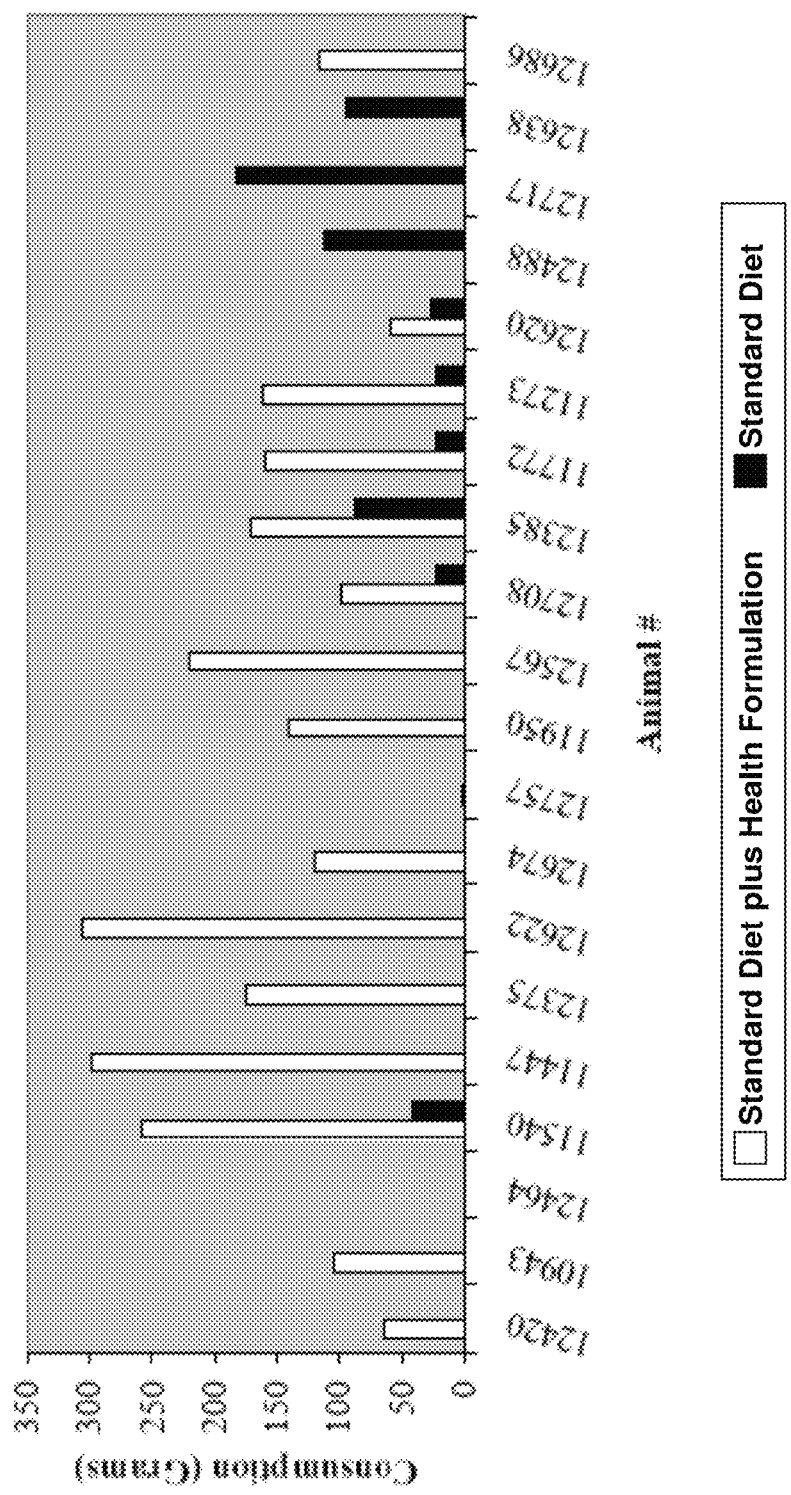
FIG. 14 graphically illustrates the amount of food consumed by the test subjects on day one of a two day study (treated, white; and untreated, black).
Figure 15:
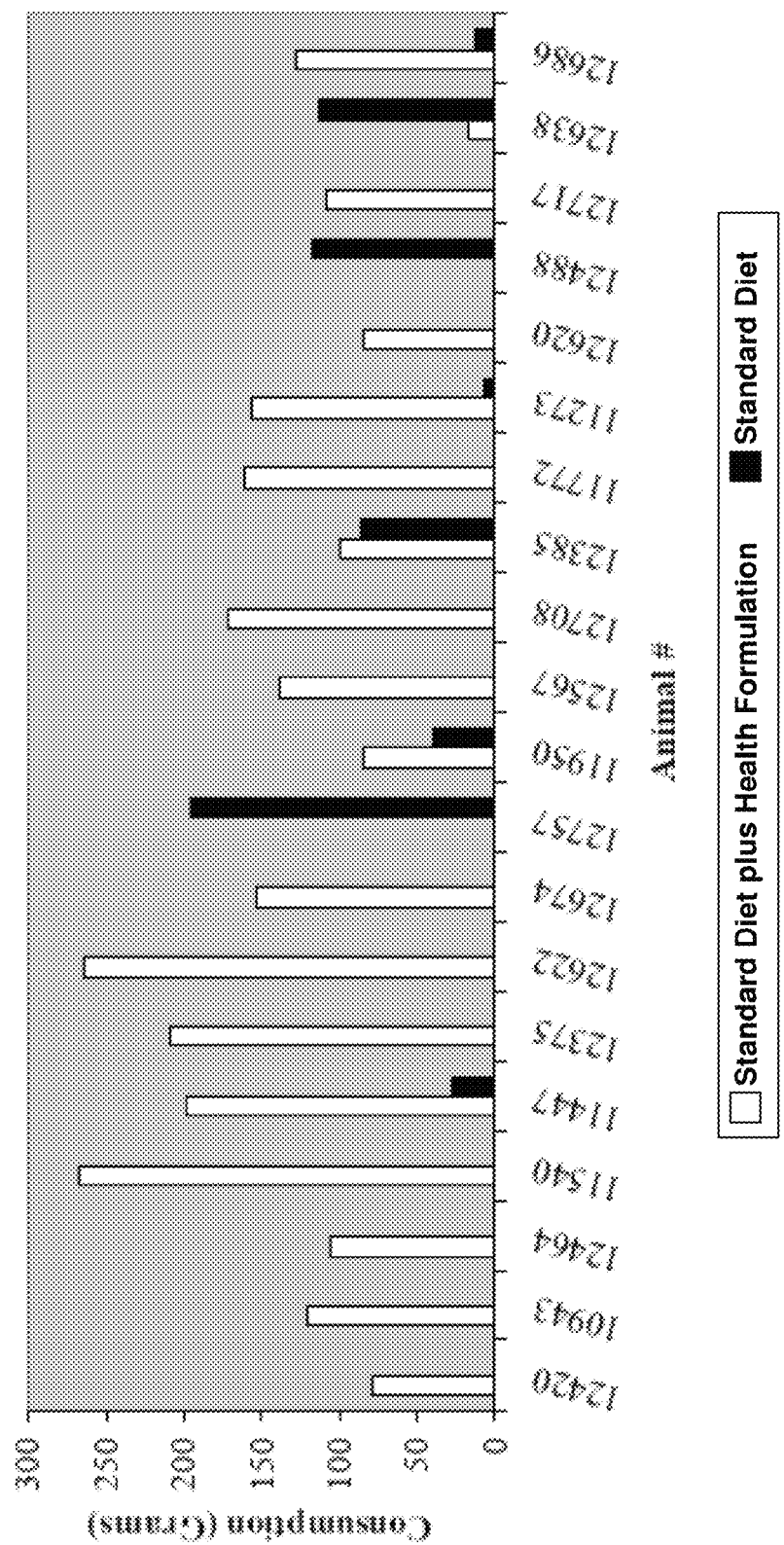
FIG. 15 graphically illustrates the amount of food consumed by the test subjects on day two of a two day study (treated, white; and untreated, black).
Figure 16:
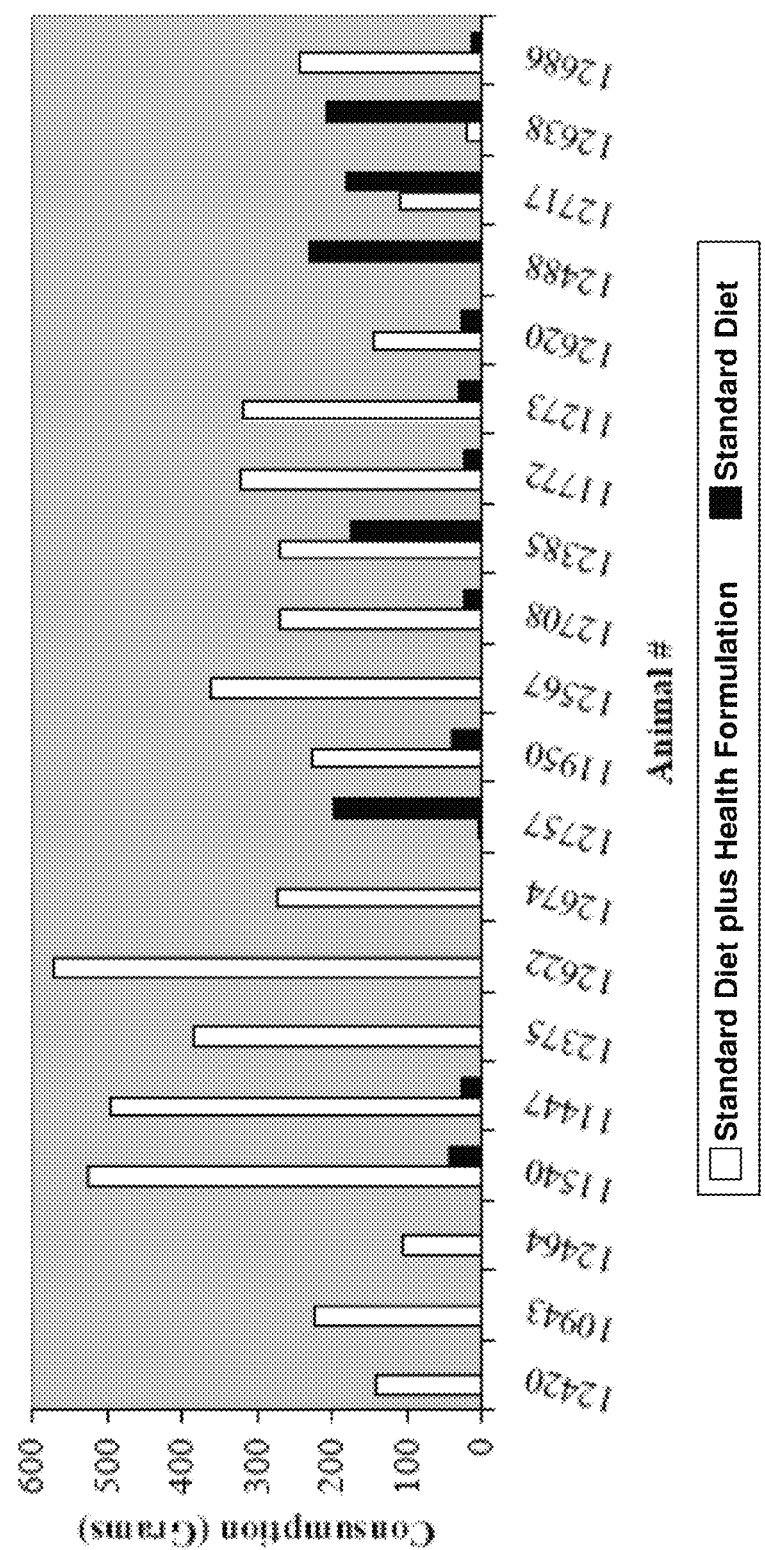
FIG. 16 graphically illustrates the total consumption of food by the test subjects over a two day study (treated, white; and untreated, black).

In the second trial, the total consumption of 20 dogs over two days was 5001 grams of the treated food (81%) and 1210 grams of the untreated food (19%). The individual consumption percentages for each dog in the trial are provided in FIG. 13. The individual consumption amounts of each food offered are provided in FIG. 14 for day 1 and FIG. 15 for day 2. Overall, the treated food was consumed 4.13 times more than the untreated food. The consumption preference included 5 dogs preferring the treated food (25%), 2 dogs preferring the untreated food (10%), and 13 dogs having no preference (65%). In regards to the first choice preference, treated food was chosen first 37 times and untreated food 3 times. Overall, the treated food was a first choice 12.33 times more than the untreated food. As an individual choice, 17 dogs chose the treated food first (85%), zero dogs chose the untreated food first (0%), and 3 dogs had no preference (15%). Of the total food consumed, the average intake ratio of each diet was 79.2% of the treated food and 20.8% of the untreated food. The average individual consumption amounts over both days are provided in FIG. 16.

Example 10

PNSB-Enhanced Microorganism Consortium Formulation Used as Cat Food Supplement

The PNSB-enhanced microorganism consortium formulation described in Example 1 may be used for the support of animal health ("Health Formulation"). In particular, the Health Formulation can be sprayed on food to be ingested by a cat.

A trial was conducted using the Health Formulation sprayed onto cat food. In particular, 3 mL of the Health Formula was sprayed onto 100 grams of standard diet cat food and fed to 20 male and female cats. Over the course of the two day trial, 6 mL total of Health Formula was presented. Two stainless steel bowls were presented to each cat on an individual basis once daily for 2 days. One bowl contained food sprayed with the Health Formulation and the other bowl contained untreated food. Bowl placement was reversed daily and both bowls were presented for 4 hours. If one food bowl was completely consumed prior to the end of the 4 hours, both bowls were removed. Food consumption and first choice preference were recorded for each cat.

The statistics applied were the Wilcoxon test to establish non-parametric ranking of observed consumption differences and an Analysis of Variance in consumption. Individual t-tests were performed to determine the consumption preference of each cat. A Chi Square test was performed to establish the significance in first choice preference.

Figure 17:
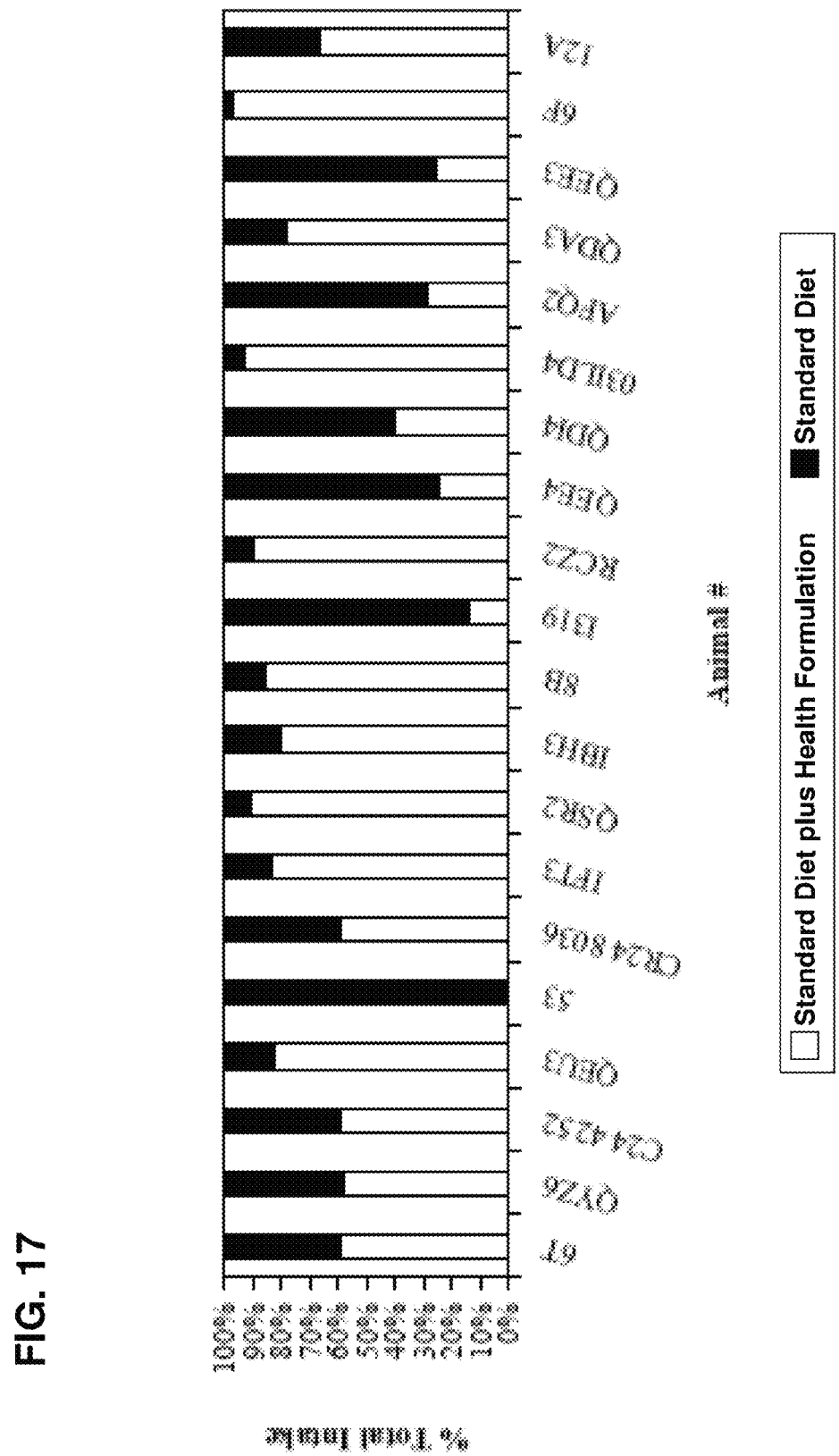
FIG. 17 graphically illustrates the percentage of treated (white) and untreated (black) food ingested by the test subjects.
Figure 18:
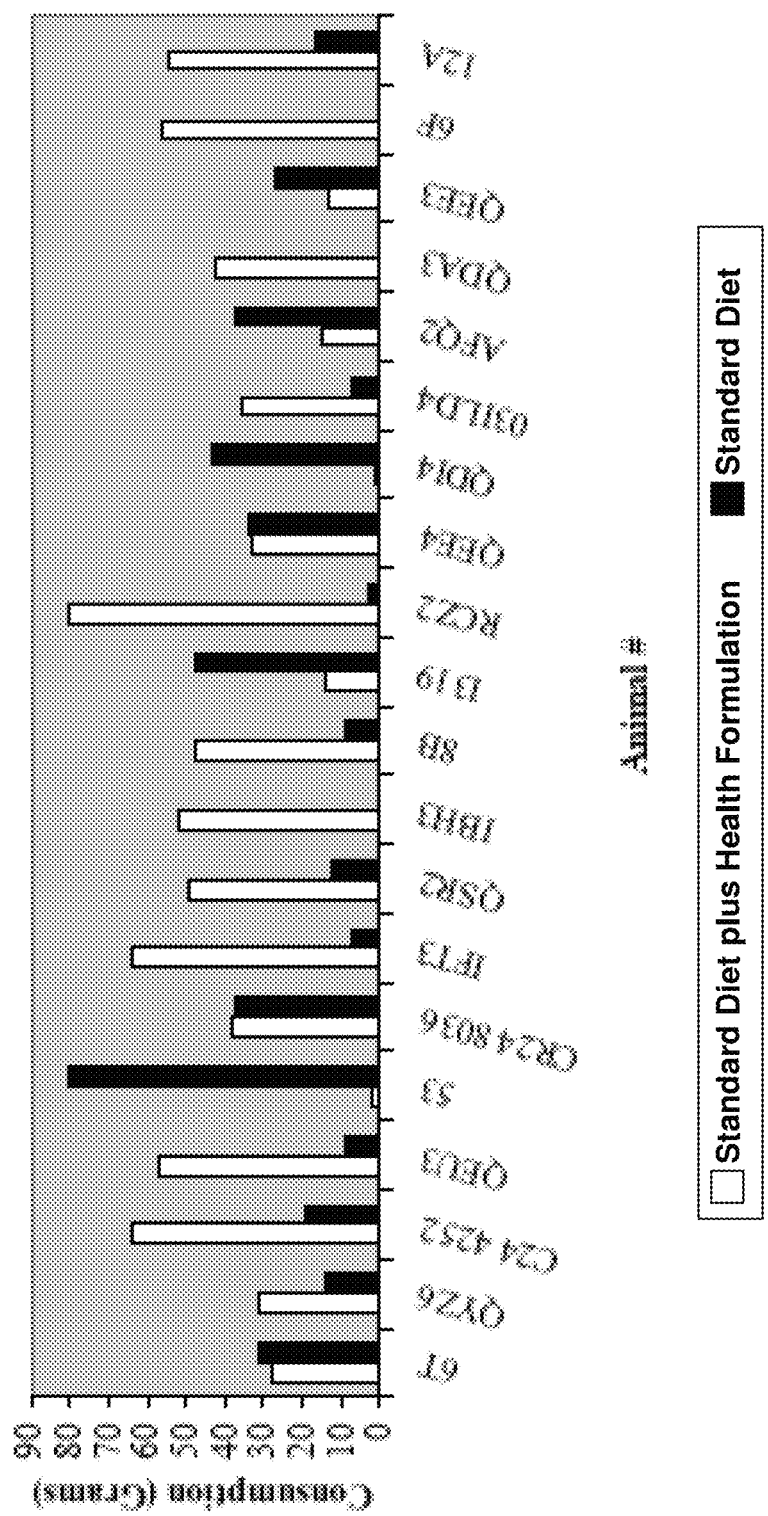
FIG. 18 graphically illustrates the amount of food consumed by the test subjects on day one of a two day study (treated, white; and untreated, black).
Figure 19:
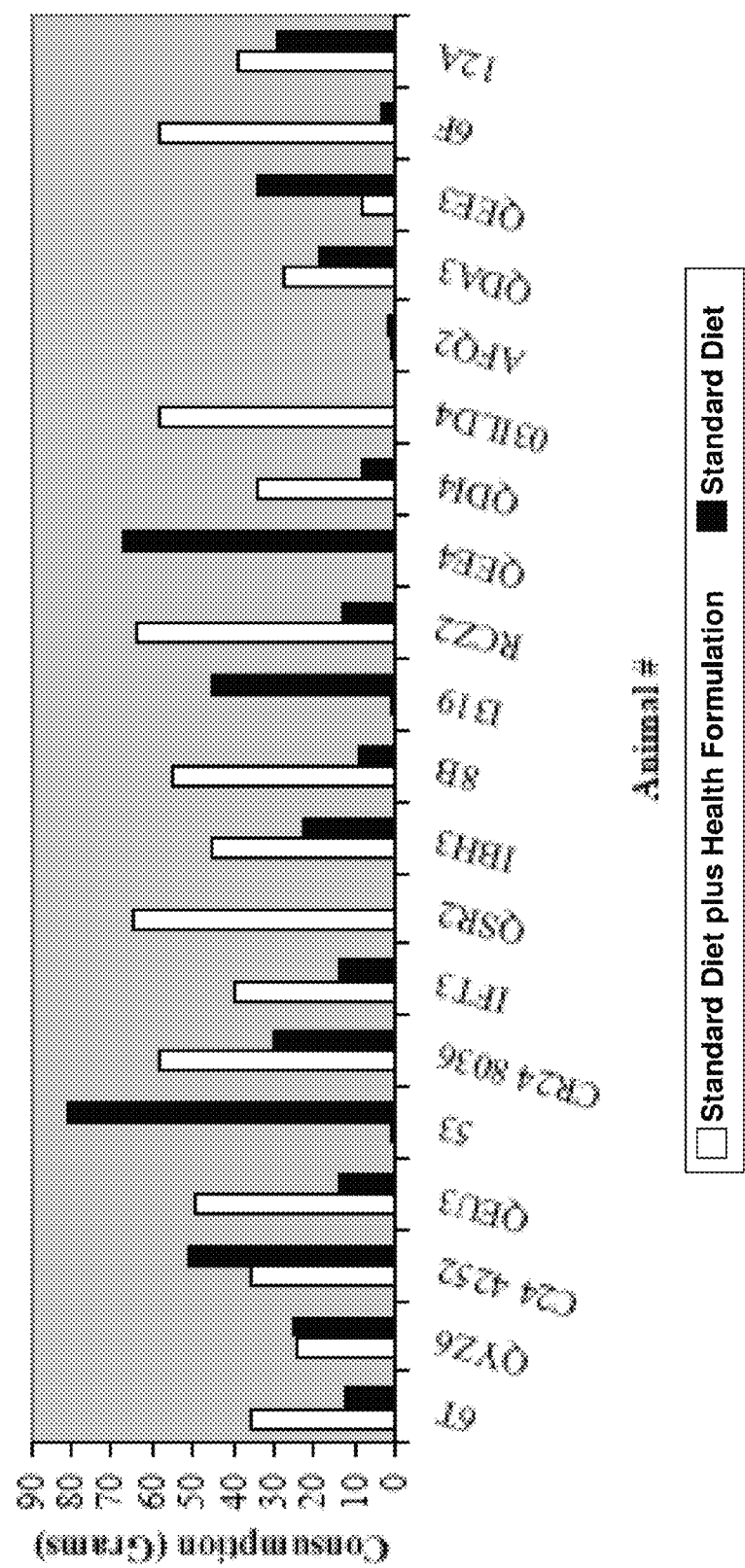
FIG. 19 graphically illustrates the amount of food consumed by the test subjects on day two of a two day study (treated, white; and untreated, black).
Figure 20:
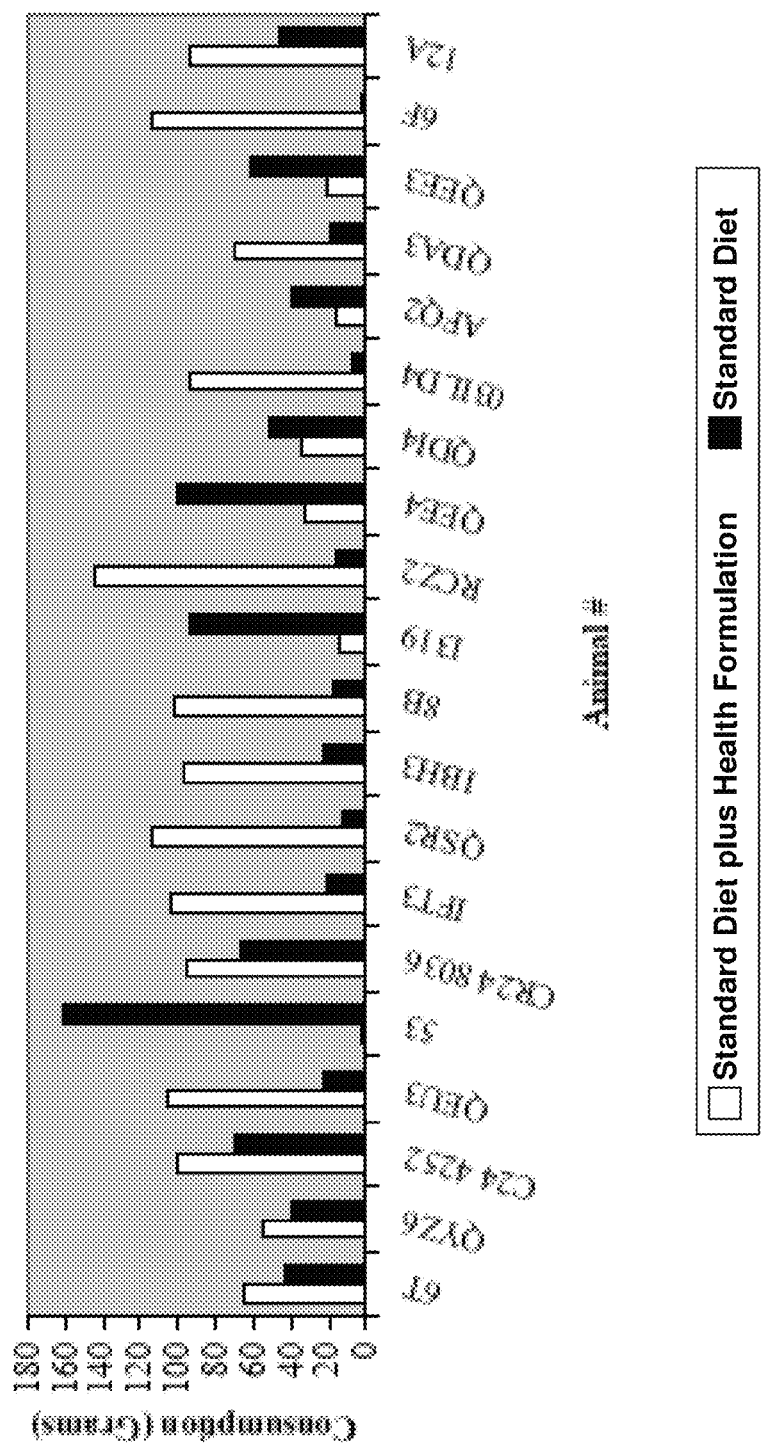
FIG. 20 graphically illustrates the total consumption of food by the test subjects over a two day study (treated, white; and untreated, black).

The total consumption of 20 cats over two days was 1477 grams of the treated food (62%) and 913 grams of the untreated food (38%). The individual consumption percentages for each cat in the trial are provided in FIG. 17. The individual consumption amounts of each food offered are provided in FIG. 18 for day 1 and FIG. 19 for day 2. Overall, the treated food was consumed 1.62 times more than the untreated food. The consumption preference included 1 cat preferring the treated food (5%), 1 cat preferring the untreated food (5%), and 18 cats having no preference (90%). In regards to the first choice preference, treated food was chosen first 25 times and untreated food 15 times. Overall, the treated food was a first choice 1.67 times more than the untreated food. As an individual choice, 6 cats chose the treated food first (30%), 1 cat chose the untreated food first (5%), and 13 cats had no preference (65%). Of the total food consumed, the average intake ratio of each diet was 61.2% of the treated food and 38.8% of the untreated food. The average individual consumption amounts over both days are provided in FIG. 20.

Example 11

PNSB-Enhanced Microorganism Consortium Formulation Used as Human Food Supplement The PNSB-enhanced microorganism consortium formulation described in Example 1 may be used for the support of human health. In particular, the formulation of Example 1 can be sprayed on food to be ingested by a human.

The invention illustratively disclosed herein suitably may be practiced in the absence of any element, which is not specifically disclosed herein. It is apparent to those skilled in the art, however, that many changes, variations, modifications, other uses, and applications to the method are possible, and also changes, variations, modifications, other uses, and applications which do not depart from the spirit and scope of the invention are deemed to be covered by the invention, which is limited only by the claims which follow.

What is claimed is:

1. A microorganism consortium starting material composition comprising:
   a. at least three microorganisms, wherein the microorganisms are co-cultured, wherein at least one microorganism is a sulfide-utilizing microorganism, wherein at least two microorganisms are selected from the group consisting of lactic acid bacteria, probiotic microorganisms, and phototrophic microorganisms; and,
   b. a carbon source, wherein the carbon source is selected from the group consisting of molasses, rum, and the combination thereof.

2. The composition of claim 1, wherein the starting material is fermented for at least 15 days to produce a fermentation product.

3. A finished product comprising the fermentation product of claim 2.

4. The composition of claim 1, wherein at least one microorganism has nucleic acid sequence having at least 90% sequence identity to SEQ ID NO:1.

5. The composition of claim 1, wherein the sulfide-utilizing microorganism is selected from the group consisting of purple non-sulfur bacteria, chromatianeae, green sulfur bacteria, colorless sulfur bacteria, filamentous green bacteria, and combinations thereof.

6. The composition of claim 1, wherein the lactic acid bacteria is selected from the group consisting of *Lactobacillus, Lactococcus, Streptococcus, Enterococcus, Pediocouss, Leuconostoc,* and combinations thereof.

7. The composition of claim 1, wherein the probiotic microorganism is selected from the group consisting of *Lactobacillus, Enterococcus, Bifidiobacterium, Bacillus, Pseudomonas, Sporolactobacillus, Micromonospora, Micrococcus, Rhodococcus, E. coli,* and combinations thereof.

8. The composition of claim 1, wherein the phototrophic microorganism is selected from the group consisting of *Rhodopseudomonas, Rodobactor, Rhodopila,* and combinations thereof.

9. The composition of claim 1, wherein the carbon source is molasses.

10. The product of claim 3, wherein the finished product further comprises molybdenum.

11. The composition of claim 1, wherein the composition further comprises acetic acid.

12. The composition of claim 11, wherein the composition further comprises an alcohol.

13. A microorganism consortium starting material composition comprising:
   a. at least three microorganisms, wherein the microorganisms are co-cultured, wherein at least one microorganism is selected from the group consisting of purple non-sulfur bacteria, chromatianeae, green sulfur bacteria, colorless sulfur bacteria, filamentous green bacteria, and combinations thereof, wherein at least two microorganisms are selected from the group consisting of *Bacillus subtilis, Bifidobacterium animalis, Bifidobacterium bifidum, Bifidobacterium longum, Enterococcus lactis, Enterococcus thermophilus, Lactobacillus acidophilus, Lactobacillus bulgaricus, Lactobacillus casei, Lactobacillus fermentum, Lactobacillus plantarum, Rhodopseudomonas palustris, Rhodopseudomonas sphaeroides, Saccharomyces cerevisiae*, and combinations thereof; and,
   b. a carbon source, wherein the carbon source is selected from the group consisting of molasses, rum, and the combination thereof.

14. The composition of claim 13, wherein the starting material is fermented for at least 15 days to produce a fermentation product.

15. A finished product comprising the fermentation product of claim 14.

16. The composition of claim 13, wherein at least one microorganism has a nucleic acid sequence having at least 90% sequence identity to SEQ ID NO:1.

17. The product of claim 13, wherein the finished product further comprises molybdenum.

18. The composition of claim 13, wherein the composition further comprises acetic acid.

19. The composition of claim 18, wherein the composition further comprises an alcohol.

20. A method of supporting the health of a recipient subject comprising administering a therapeutically effective amount of a finished product to the recipient subject, wherein the finished product comprises:
   a. a starting material solution comprising at least three microorganisms, wherein the microorganisms are co-cultured, wherein at least one microorganism is selected from the group consisting of purple non-sulfur bacteria, chromatianeae, green sulfur bacteria, colorless sulfur bacteria, filamentous green bacteria, and combinations thereof, and wherein at least two microorganisms are selected from the group consisting of *Bacillus subtilis, Bifidobacterium animalis, Bifidobacterium bifidum, Bifidobacterium longum, Enterococcus lactis, Enterococcus thermophilus, Lactobacillus acidophilus, Lactobacillus bulgaricus, Lactobacillus casei, Lactobacillus fermentum, Lactobacillus plantarum, Rhodopseudomonas palustris, Rhodopseudomonas sphaeroides, Saccharomyces cerevisiae*, and combinations thereof; and,
   b. a carbon source, wherein the carbon source is selected from the group consisting of molasses, rum, and the combination thereof.

21. The method of claim 20, wherein the starting material is fermented for at least 15 days to produce a fermentation product.

22. The method of claim 21, wherein the fermentation product is included in said finished product.

23. The method of claim 22, wherein the finished product is included in food ingested by the subject.

24. The method of claim 22, wherein the finished product is included in water ingested by the subject.

25. The method of claim 22, wherein the finished product is administered to the oral cavity of the subject.

26. The method of claim 20, wherein at least one microorganism has a nucleic acid sequence having at least 90% sequence identity to SEQ ID NO:1.

27. The method of claim 20, wherein the carbon source is molasses.

28. The method of claim 22, wherein the finished product is an aqueous solution.

29. A method of enhancing the health of a plant comprising administering a therapeutically effective amount of a finished product to the recipient plant or seed, wherein the finished product comprises:
   a. a starting material solution comprising at least three microorganisms, wherein the microorganisms are co-cultured, wherein at least one microorganism is selected from the group consisting of purple non-sulfur bacteria, chromatianeae, green sulfur bacteria, colorless sulfur bacteria, filamentous green bacteria, and combinations thereof, and wherein at least two microorganisms are selected from the group consisting of *Bacillus subtilis, Bifidobacterium animalis, Bifidobacterium bifidum, Bifidobacterium longum, Enterococcus lactis, Enterococcus thermophilus, Lactobacillus acidophilus, Lactobacillus bulgaricus, Lactobacillus casei, Lactobacillus fermentum, Lactobacillus plantarum, Rhodopseudomonas palustris, Rhodopseudomonas sphaeroides, Saccharomyces cerevisiae*, and combinations thereof; and,
   b. a carbon source, wherein the carbon source is selected from the group consisting of molasses, rum, and the combination thereof.

30. The method of claim 29, wherein the starting material is fermented for at least 15 days to produce a fermentation product.

31. The method of claim 30, wherein the fermentation product is included in said finished product.

32. The method of claim 31, wherein the finished product is administered to the soil of the plant or seed.

33. The method of claim 31, wherein the finished product is administered to the water source of the plant or seed.

34. The method of claim 29, wherein at least one microorganism has a nucleic acid sequence having at least 90% sequence identity to SEQ ID NO:1.

35. The method of claim 31, wherein the finished product is an aqueous solution.

\* \* \* \* \*

SEQUENCE LISTING

```
<160> NUMBER OF SEQ ID NOS: 1

<210> SEQ ID NO 1
<211> LENGTH: 1366
<212> TYPE: DNA
<213> ORGANISM: Phaeospirillum sp.
<220> FEATURE:
```

-continued

```
<221> NAME/KEY: misc_feature
<223> OTHER INFORMATION: Organism is closest relative to Phaeospirillum
      sp.

<400> SEQUENCE: 1
ttacacatgc aagtcgaacg ccccgcaagg ggagtggcgc acgggtgagt aacgcgtggg        60
aacctaccta tcggtacgga ataacacagg gaaacttgtg ctaataccgt atgagctcta      120
cggaggaaag atttatcgcc gatagatggg cccgcgtccg attagctagt tggtgaggta      180
acggctcacc aaggcttcga tcggtagctg gtctgagagg atgatcagcc acactgggac      240
tgagacacgg cccagactcc tacgggaggc agcagtgggg aatattggac aatgggcgca      300
agcctgatcc agccatgccg cgtgagtgat gaaggcctta ggttgtaaa gctctttcgt       360 cggggaagat aatgacggta cccgaagaag aagcctcggc taactccgtg ccagcagccg      420
cggtaagacg gaggaggcta gcgttgttcg gaattactgg gcgtaaagcg tacgcaggcg      480
gttgatcaag tcaggtgtga agcccgggg ctcaacctcg gaattgcgcc tgagactggt       540
cggctagagt tcggaagagg agagtggaat tcccagtgta gaggtgaaat tcgtagatat      600
tgggaagaac accagtggcg aaggcgactc tctggtccga tactgacgct caagtacgaa      660
agcgtgggga gcaaacagga ttagataccc tggtagtcca cgccgtaaac gatgtgtgct      720
agatgtcgga aagcttgctt ttcggtgtcg cagctaacgc gataagcaca ccgcctgggg      780
agtacggccg caaggttaaa actcaaagga attgacgggg gcccgcacaa gcggtggagc      840
atgtggttta attcgaagca acgcgcagaa ccttaccagc tcttgacatg gaagtatgg       900 gcctgagaga tcgggttctt cagttcggct ggcttccaca caggtgctgc atggctgtcg      960
tcagctcgtg tcgtgagatg ttgggttaag tcccgcaacg agcgcaaccc tcgccttcag     1020
ttgccatcac gtctgggtgg gcactctgaa ggaactgccg gtgacaagcc ggaggaaggt     1080
ggggatgacg tcaagtcctc atggccctta tgggctgggc tacacacgtg ctacaatggc     1140
ggtgacaatg ggccgcgaag gggcgacctg gagcgaatcc ccaaaaaccg tctcagttcg     1200
gattgcactc tgcaactcgg gtgcatgaag tcggaatcgc tagtaatcgt ggatcagcac     1260
gccacggtga atacgttccc gggccttgta cacaccgccc gtcacaccat gggagttggt     1320
tctaccttaa gccggtgcgc taaccgcaag gaggcagccg accacg                    1366
```